United States Patent
Henderson et al.

(10) Patent No.: US 11,278,661 B2
(45) Date of Patent: Mar. 22, 2022

(54) INFUSION SYSTEM AND COMPONENTS THEREOF

(71) Applicant: Beta Bionics, Inc., Concord, MA (US)

(72) Inventors: David Matthew Henderson, Mission Viejo, CA (US); Todd S. Ray, Spokane Valley, WA (US); Michael J. Rosinko, Anaheim, CA (US); Bryan Dale Knodel, Flagstaff, AZ (US)

(73) Assignee: BETA BIONICS, INC., Concord, MA (US)

( * ) Notice: Subject to any disclaimer, the term of this patent is extended or adjusted under 35 U.S.C. 154(b) by 0 days.

(21) Appl. No.: 16/814,925

(22) Filed: Mar. 10, 2020

(65) Prior Publication Data
US 2021/0283328 A1  Sep. 16, 2021

(51) Int. Cl.
| | |
|---|---|
| *A61M 5/14* | (2006.01) |
| *A61M 5/142* | (2006.01) |
| *A61M 5/162* | (2006.01) |
| *A61M 39/24* | (2006.01) |
| *A61M 5/172* | (2006.01) |

(52) U.S. Cl.
CPC .......... *A61M 5/1407* (2013.01); *A61M 5/142* (2013.01); *A61M 5/162* (2013.01); *A61M 5/1723* (2013.01); *A61M 39/24* (2013.01); *A61M 2205/8206* (2013.01); *A61M 2205/8243* (2013.01)

(58) Field of Classification Search
CPC ...... A61M 5/1407; A61M 5/142; A61M 5/14; A61M 60/871; A61M 60/873; A61M 60/80; A61M 2205/82; A61M 2205/86; A61M 2205/8237; A61M 2205/8243; A61M 2205/8256; H01F 2003/005; H01F 2005/027; H01F 38/14
See application file for complete search history.

(56) References Cited

U.S. PATENT DOCUMENTS

| | | |
|---|---|---|
| 1,930,929 A | 10/1933 | Eisenberg |
| 3,807,467 A | 4/1974 | Tascher et al. |
| 4,150,673 A | 4/1979 | Watt |
| 4,253,501 A | 3/1981 | Ogle |

(Continued)

FOREIGN PATENT DOCUMENTS

| | | |
|---|---|---|
| EP | 3 150 241 | 6/2018 |
| EP | 3 378 516 | 9/2018 |

(Continued)

OTHER PUBLICATIONS

Kolind et al., "Preservation-free drug for insulin pumps," Novo Nordisk Pharmaceutical company, Pump partner meeting ATTD 2020, WOP Technology Presentation, 26 pages.

(Continued)

*Primary Examiner* — Jason E Flick
(74) *Attorney, Agent, or Firm* — Knobbe, Martens, Olson & Bear LLP

(57) ABSTRACT

Certain embodiments provide multi-medicament infusion systems for preventing the cross-channeling of medicaments. The system may include one or more of an infusion pump, medicament cartridges, cartridge connectors, a multi-channel fluid conduit, and an infusion set. The infusion pump can have an inductively chargeable battery assembly that can be charged by an inductive charging pad.

20 Claims, 33 Drawing Sheets

(56) References Cited

U.S. PATENT DOCUMENTS

| | | |
|---|---|---|
| 4,515,584 A | 5/1985 | Abe et al. |
| 4,585,439 A | 4/1986 | Michel |
| 4,608,042 A | 8/1986 | Vanderveen |
| 4,675,006 A | 6/1987 | Hrushesky |
| 5,085,643 A | 2/1992 | Larkin et al. |
| 5,243,982 A | 9/1993 | Mostl |
| 5,298,023 A | 3/1994 | Haber |
| 5,356,380 A | 10/1994 | Hoekwater et al. |
| 5,411,480 A | 5/1995 | Kriesel |
| 5,472,403 A | 12/1995 | Cornacchia |
| 5,505,704 A | 4/1996 | Pawelka et al. |
| 5,522,803 A | 6/1996 | Teissen-Simony |
| 5,545,152 A | 8/1996 | Funderburk |
| 5,616,124 A | 4/1997 | Hague et al. |
| 5,916,494 A | 6/1999 | Widman et al. |
| 5,954,697 A | 9/1999 | Srisathapat et al. |
| 5,961,494 A | 10/1999 | Hogan |
| 5,971,972 A | 10/1999 | Rosenbaum |
| 6,106,498 A | 8/2000 | Friedli et al. |
| 6,132,416 A | 10/2000 | Broselow |
| 6,248,067 B1 | 6/2001 | Causey, III et al. |
| 6,259,587 B1 | 7/2001 | Sheldon et al. |
| 6,360,784 B1 | 3/2002 | Philippens et al. |
| 6,362,591 B1 | 3/2002 | Moberg |
| 6,368,314 B1 | 4/2002 | Kipfer et al. |
| 6,390,130 B1 | 5/2002 | Guala |
| 6,485,465 B2 | 11/2002 | Moberg et al. |
| 6,551,276 B1 | 4/2003 | Mann et al. |
| 6,551,298 B1 | 4/2003 | Zhang et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,572,545 B2 | 6/2003 | Knobbe et al. |
| 6,585,695 B1 | 7/2003 | Adair et al. |
| 6,620,138 B1 | 9/2003 | Marrgi et al. |
| 6,641,533 B2 | 11/2003 | Causey, III et al. |
| 6,652,483 B2 | 11/2003 | Slate |
| 6,656,148 B2 | 12/2003 | Das et al. |
| 6,659,980 B2 | 12/2003 | Moberg et al. |
| 6,719,728 B2 | 4/2004 | Mason et al. |
| 6,736,797 B1 | 5/2004 | Larsen et al. |
| 6,752,787 B1 | 6/2004 | Causey, III et al. |
| 6,801,420 B2 | 10/2004 | Talbot et al. |
| 6,809,653 B1 | 10/2004 | Mann et al. |
| 6,811,534 B2 | 11/2004 | Bowman et al. |
| 6,821,421 B2 | 11/2004 | Murakami |
| 6,854,620 B2 | 2/2005 | Ramey |
| 6,872,200 B2 | 3/2005 | Mann et al. |
| 6,878,132 B2 | 4/2005 | Kipfer |
| 6,936,029 B2 | 8/2005 | Mann et al. |
| 6,939,329 B1 | 9/2005 | Verkaart |
| 6,958,705 B2 | 10/2005 | Lebel et al. |
| 6,960,198 B2 | 11/2005 | Sarmiento |
| 6,979,326 B2 | 12/2005 | Mann et al. |
| 6,997,920 B2 | 2/2006 | Mann et al. |
| 7,025,226 B2 | 4/2006 | Ramey |
| 7,025,743 B2 | 4/2006 | Mann et al. |
| 7,098,803 B2 | 8/2006 | Mann et al. |
| 7,109,878 B2 | 9/2006 | Mann et al. |
| 7,187,528 B2 | 3/2007 | Talbot et al. |
| 7,193,521 B2 | 3/2007 | Moberg et al. |
| 7,281,314 B2 | 10/2007 | Hess et al. |
| 7,285,105 B2 | 10/2007 | Kim et al. |
| 7,291,133 B1 | 11/2007 | Kindler et al. |
| 7,324,012 B2 | 1/2008 | Mann et al. |
| 7,342,508 B2 | 3/2008 | Morgan et al. |
| 7,460,350 B2 | 12/2008 | Talbot et al. |
| 7,534,226 B2 | 5/2009 | Mernoe et al. |
| 7,602,310 B2 | 10/2009 | Mann et al. |
| 7,621,893 B2 | 11/2009 | Moberg et al. |
| 7,625,354 B2 | 12/2009 | Hochman |
| 7,628,772 B2 | 12/2009 | McConnell et al. |
| 7,628,782 B2 | 12/2009 | Adair et al. |
| 7,648,494 B2 | 1/2010 | Kornerup et al. |
| 7,654,127 B2 | 2/2010 | Krulevitch et al. |
| 7,655,618 B2 | 2/2010 | Green et al. |
| 7,658,734 B2 | 2/2010 | Adair et al. |
| 7,678,762 B2 | 3/2010 | Green et al. |
| 7,678,763 B2 | 3/2010 | Green et al. |
| 7,683,027 B2 | 3/2010 | Green et al. |
| 7,708,717 B2 | 5/2010 | Estes et al. |
| 7,760,481 B2 | 7/2010 | Talbot et al. |
| 7,766,873 B2 | 8/2010 | Moberg et al. |
| 7,776,030 B2 | 8/2010 | Estes et al. |
| 7,789,859 B2 | 9/2010 | Estes et al. |
| 7,794,427 B2 | 9/2010 | Estes et al. |
| 7,794,428 B2 | 9/2010 | Estes et al. |
| 7,815,602 B2 | 10/2010 | Mann et al. |
| 7,819,843 B2 | 10/2010 | Mann et al. |
| 7,831,310 B2 | 11/2010 | Lebel et al. |
| 7,833,196 B2 | 11/2010 | Estes et al. |
| 7,879,010 B2 | 2/2011 | Hunn et al. |
| 7,879,026 B2 | 2/2011 | Estes et al. |
| 7,887,512 B2 | 2/2011 | Estes et al. |
| 7,892,206 B2 | 2/2011 | Moberg et al. |
| 7,914,449 B2 | 3/2011 | Kouchi et al. |
| 7,922,708 B2 | 4/2011 | Estes et al. |
| 7,951,112 B2 | 5/2011 | Patzer |
| 7,967,785 B2 | 6/2011 | Morgan et al. |
| 7,981,084 B2 | 7/2011 | Estes et al. |
| 7,981,105 B2 | 7/2011 | Adair et al. |
| 7,988,683 B2 | 8/2011 | Adair et al. |
| 7,998,111 B2 | 8/2011 | Moberg et al. |
| 7,998,131 B2 | 8/2011 | Adair et al. |
| 8,004,422 B2 | 8/2011 | Hess et al. |
| 7,938,803 B2 | 10/2011 | Mernoe et al. |
| 8,034,026 B2 | 10/2011 | Grant et al. |
| 8,057,436 B2 | 11/2011 | Causey et al. |
| 8,062,257 B2 | 11/2011 | Moberg et al. |
| 8,065,096 B2 | 11/2011 | Moberg et al. |
| 8,088,096 B2 | 1/2012 | Lauchard et al. |
| 8,105,279 B2 | 1/2012 | Mernoe et al. |
| 8,106,534 B2 | 1/2012 | Spurlin et al. |
| 8,142,397 B2 | 3/2012 | Patzer |
| 8,167,846 B2 | 5/2012 | Chong et al. |
| 8,177,767 B2 | 5/2012 | Kristensen et al. |
| 8,182,447 B2 | 5/2012 | Moberg et al. |
| 8,192,394 B2 | 6/2012 | Estes et al. |
| 8,197,444 B1 | 6/2012 | Bazargan et al. |
| 8,206,350 B2 | 6/2012 | Mann et al. |
| 8,206,353 B2 | 6/2012 | Chong et al. |
| 8,211,059 B2 | 7/2012 | Kriesel |
| 8,211,062 B2 | 7/2012 | Estes et al. |
| 8,251,959 B2 | 8/2012 | Johner et al. |
| 8,257,345 B2 | 9/2012 | Adair et al. |
| 8,267,893 B2 | 9/2012 | Moberg et al. |
| 8,273,061 B2 | 9/2012 | McConnell et al. |
| 8,282,601 B2 | 10/2012 | Mernoe et al. |
| 8,287,495 B2 | 10/2012 | Michaud et al. |
| 8,287,516 B2 | 10/2012 | Kornerup et al. |
| 8,298,184 B2 | 10/2012 | DiPerna et al. |
| 8,303,572 B2 | 11/2012 | Adair et al. |
| 8,372,039 B2 | 2/2013 | Mernoe et al. |
| 8,409,142 B2 | 4/2013 | Causey et al. |
| 8,430,847 B2 | 4/2013 | Mernoe et al. |
| 8,430,849 B2 | 4/2013 | Smith et al. |
| 8,454,575 B2 | 6/2013 | Estes et al. |
| 8,469,942 B2 | 6/2013 | Kow et al. |
| 8,475,408 B2 | 7/2013 | Mernoe et al. |
| 8,480,623 B2 | 7/2013 | Mernoe et al. |
| 8,483,980 B2 | 7/2013 | Moberg et al. |
| 8,500,716 B2 | 8/2013 | Adair et al. |
| 8,512,276 B2 | 8/2013 | Talbot et al. |
| 8,512,289 B2 | 8/2013 | Chong et al. |
| 8,523,803 B1 | 9/2013 | Favreau |
| 8,551,045 B2 | 10/2013 | Sie et al. |
| 8,551,046 B2 | 10/2013 | Causey et al. |
| 8,556,856 B2 | 10/2013 | Bazargan et al. |
| 8,556,866 B2 | 10/2013 | Krulevitch et al. |
| 8,562,565 B2 | 10/2013 | Fonacier et al. |
| 8,562,587 B2 | 10/2013 | Kovatchev et al. |
| 8,568,349 B2 | 10/2013 | Shergold |
| 8,573,027 B2 | 11/2013 | Rosinko et al. |
| 8,579,813 B2 | 11/2013 | Causey, III et al. |

(56) References Cited

U.S. PATENT DOCUMENTS

| | | |
|---|---|---|
| 8,597,269 B2 | 12/2013 | Chong et al. |
| 8,603,026 B2 | 12/2013 | Favreau |
| 8,603,027 B2 | 12/2013 | Favreau |
| 8,603,033 B2 | 12/2013 | Bazargan et al. |
| 8,613,726 B2 | 12/2013 | Causey, III et al. |
| 8,613,731 B2 | 12/2013 | Hansen et al. |
| 8,617,110 B2 | 12/2013 | Moberg et al. |
| 8,622,966 B2 | 1/2014 | Causey, III et al. |
| 8,628,510 B2 | 1/2014 | Bazargan et al. |
| 8,641,671 B2 | 2/2014 | Michaud et al. |
| 8,647,074 B2 | 2/2014 | Moberg et al. |
| 8,647,296 B2 | 2/2014 | Moberg et al. |
| 8,663,103 B2 | 3/2014 | Causey, III et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,696,633 B2 | 4/2014 | Estes et al. |
| 8,747,368 B2 | 6/2014 | Mernoe et al. |
| 8,747,369 B2 | 6/2014 | Mernoe et al. |
| 8,758,323 B2 | 6/2014 | Michaud et al. |
| 8,771,229 B2 | 7/2014 | Amirouche et al. |
| 8,777,901 B2 | 7/2014 | Smith et al. |
| 8,790,307 B2 | 7/2014 | Amirouche et al. |
| 8,821,442 B2 | 9/2014 | Haaar |
| 8,823,528 B2 | 9/2014 | Blomquist |
| 8,834,420 B2 | 9/2014 | Estes et al. |
| 8,841,012 B2 | 9/2014 | Fonacier et al. |
| 8,864,726 B2 | 10/2014 | Halili et al. |
| 8,864,737 B2 | 10/2014 | Hasegawa et al. |
| 8,864,739 B2 | 10/2014 | Moberg et al. |
| 8,870,829 B2 | 10/2014 | Halili et al. |
| 8,876,770 B2 | 11/2014 | Kraft et al. |
| 8,900,206 B2 | 12/2014 | Halili et al. |
| 8,905,972 B2 | 12/2014 | Smith et al. |
| 8,915,879 B2 | 12/2014 | Smith et al. |
| 8,936,573 B2 | 1/2015 | Blomquist |
| 8,945,068 B2 | 2/2015 | Halili et al. |
| 8,974,435 B2 | 3/2015 | Friedli |
| 8,992,475 B2 | 3/2015 | Mann et al. |
| 8,992,507 B2 | 3/2015 | Aeschlimann et al. |
| 8,998,840 B2 | 4/2015 | Hanson et al. |
| 8,998,842 B2 | 4/2015 | Lauchard et al. |
| 8,998,858 B2 | 4/2015 | Chong et al. |
| 9,011,371 B2 | 4/2015 | Moberg et al. |
| 9,033,925 B2 | 5/2015 | Moberg et al. |
| 9,033,951 B2 | 5/2015 | Kow et al. |
| 9,050,406 B2 | 6/2015 | Kow et al. |
| 9,101,710 B2 | 8/2015 | Yavorsky et al. |
| 9,101,715 B2 | 8/2015 | Causey, III et al. |
| 9,107,999 B2 | 8/2015 | Moberg et al. |
| 9,114,209 B2 | 8/2015 | Estes et al. |
| 9,114,213 B2 | 8/2015 | Murakami et al. |
| 9,119,917 B2 | 9/2015 | Blomquist |
| 9,132,228 B2 | 9/2015 | Yan |
| 9,173,998 B2 | 11/2015 | Rosinko et al. |
| 9,180,242 B2 | 11/2015 | Metzmaker et al. |
| 9,180,243 B2 | 11/2015 | Michaud |
| 9,180,254 B2 | 11/2015 | Avery |
| 9,184,490 B2 | 11/2015 | Crouther et al. |
| 9,194,388 B2 | 11/2015 | Laermer |
| 9,205,192 B2 | 12/2015 | Estes et al. |
| 9,211,376 B2 | 12/2015 | Kouyoumjian et al. |
| 9,211,377 B2 | 12/2015 | DiPerna et al. |
| 9,216,249 B2 | 12/2015 | Smith et al. |
| 9,220,835 B2 | 12/2015 | Cane' |
| 9,250,106 B2 | 2/2016 | Rosinko et al. |
| 9,272,009 B2 | 3/2016 | Spencer |
| 9,283,318 B2 | 3/2016 | Yavorsky et al. |
| 9,295,826 B2 | 3/2016 | Bertrand et al. |
| 9,308,320 B2 | 4/2016 | Smith et al. |
| 9,308,321 B2 | 4/2016 | Alderete et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,335,910 B2 | 5/2016 | Farnan et al. |
| 9,339,639 B2 | 5/2016 | Halili et al. |
| 9,344,024 B2 | 5/2016 | Favreau |
| 9,345,643 B2 | 5/2016 | Okiyama |
| 9,364,608 B2 | 6/2016 | Moberg et al. |
| 9,379,652 B2 | 6/2016 | Favreau |
| 9,379,653 B2 | 6/2016 | Favreau |
| 9,381,297 B2 | 7/2016 | Brown et al. |
| 9,381,300 B2 | 7/2016 | Smith et al. |
| 9,393,399 B2 | 7/2016 | Yavorsky et al. |
| 9,415,157 B2 | 8/2016 | Mann et al. |
| 9,427,519 B2 | 8/2016 | Kraft et al. |
| 9,433,731 B2 | 9/2016 | Track et al. |
| 9,433,732 B2 | 9/2016 | Moberg et al. |
| 9,433,733 B2 | 9/2016 | Moberg et al. |
| 9,452,255 B2 | 9/2016 | Tieck et al. |
| 9,452,256 B2 | 9/2016 | Tieck et al. |
| 9,463,309 B2 | 10/2016 | Yavorsky et al. |
| 9,494,147 B2 | 11/2016 | Chong et al. |
| 9,498,573 B2 | 11/2016 | Smith et al. |
| 9,514,518 B2 | 12/2016 | Gillespie et al. |
| 9,517,299 B2 | 12/2016 | Tieck et al. |
| 9,517,301 B2 | 12/2016 | Estes et al. |
| 9,533,132 B2 | 1/2017 | Halili et al. |
| 9,539,385 B2 | 1/2017 | Mathys |
| 9,539,388 B2 | 1/2017 | Causey et al. |
| 9,554,967 B2 | 1/2017 | Moia et al. |
| 9,579,452 B2 | 2/2017 | Adair et al. |
| 9,592,339 B2 | 3/2017 | Zhou |
| 9,597,462 B2 | 3/2017 | Moore |
| 9,610,431 B2 | 4/2017 | Halili et al. |
| 9,629,992 B2 | 4/2017 | Halili et al. |
| 9,636,453 B2 | 5/2017 | Monirabbasi et al. |
| 9,682,189 B2 | 6/2017 | Good et al. |
| 9,687,612 B2 | 6/2017 | Avery et al. |
| 9,715,327 B2 | 7/2017 | Rosinko et al. |
| 9,717,845 B2 | 8/2017 | Istoc |
| 9,717,848 B2 | 8/2017 | Geismar et al. |
| 9,731,067 B2 | 8/2017 | Pananen |
| 9,744,290 B2 | 8/2017 | Tieck et al. |
| 9,744,291 B2 | 8/2017 | Tieck et al. |
| 9,744,301 B2 | 8/2017 | Mann et al. |
| 9,750,871 B2 | 9/2017 | Metzmaker et al. |
| 9,750,873 B2 | 9/2017 | Brown et al. |
| 9,750,875 B2 | 9/2017 | Smith et al. |
| 9,770,553 B2 | 9/2017 | Bazargan et al. |
| 9,782,543 B2 | 10/2017 | Groeschke et al. |
| 9,789,245 B2 | 10/2017 | Tieck et al. |
| 9,795,732 B2 | 10/2017 | Track et al. |
| 9,801,787 B2 | 10/2017 | Py |
| 9,814,830 B2 | 11/2017 | Mernoe et al. |
| 9,814,872 B2 | 11/2017 | Eggert et al. |
| 9,839,741 B2 | 12/2017 | Yavorsky et al. |
| 9,841,014 B2 | 12/2017 | Yap et al. |
| 9,863,837 B2 | 1/2018 | Rule et al. |
| 9,872,957 B2 | 1/2018 | Causey et al. |
| 9,883,834 B2 | 2/2018 | Amirouche et al. |
| 9,889,256 B2 | 2/2018 | Cabiri et al. |
| 9,895,490 B2 | 2/2018 | Kow et al. |
| 9,925,330 B2 | 3/2018 | Tieck et al. |
| 9,931,459 B2 | 4/2018 | Tieck et al. |
| 9,931,460 B2 | 4/2018 | Tieck et al. |
| 9,943,645 B2 | 4/2018 | Monirabbasi et al. |
| 9,950,113 B2 | 4/2018 | Franke et al. |
| 9,987,420 B2 | 6/2018 | Pananen |
| 9,993,592 B2 | 6/2018 | Amirouche et al. |
| 9,993,594 B2 | 6/2018 | Bazargan et al. |
| 10,010,674 B2 | 7/2018 | Rosinko et al. |
| 10,010,678 B2 | 7/2018 | Schildt et al. |
| 10,016,564 B2 | 7/2018 | Piehl et al. |
| 10,029,045 B2 | 7/2018 | Smith et al. |
| 10,064,993 B2 | 9/2018 | Mernoe et al. |
| 10,071,200 B2 | 9/2018 | Alderete et al. |
| 10,080,839 B2 | 9/2018 | Cole et al. |
| 10,086,133 B2 | 10/2018 | Pananen et al. |
| 10,086,134 B2 | 10/2018 | Pananen et al. |
| 10,092,701 B2 | 10/2018 | Johansen et al. |
| 10,105,483 B2 | 10/2018 | Mernoe |
| 10,105,497 B2 | 10/2018 | Dreier et al. |
| 10,130,759 B2 | 11/2018 | Amirouche et al. |

(56) References Cited

U.S. PATENT DOCUMENTS

| | | |
|---|---|---|
| 10,130,763 B2 | 11/2018 | Lauchard et al. |
| 10,137,243 B2 | 11/2018 | Wang et al. |
| 10,141,882 B2 | 11/2018 | Favreau |
| 10,146,911 B2 | 12/2018 | Track |
| 10,166,327 B2 | 1/2019 | Tieck et al. |
| 10,172,998 B2 | 1/2019 | Tieck et al. |
| 10,172,999 B2 | 1/2019 | Tieck et al. |
| 10,207,047 B2 | 2/2019 | Estes |
| 10,213,549 B2 | 2/2019 | Amirouche et al. |
| 10,220,143 B2 | 3/2019 | Moberg et al. |
| 10,228,663 B2 | 3/2019 | Favreau |
| 10,232,109 B2 | 3/2019 | Deak et al. |
| 10,238,030 B2 | 3/2019 | Urbani |
| 10,238,793 B2 | 3/2019 | Deak et al. |
| 10,252,001 B2 | 4/2019 | Geismar et al. |
| 10,258,736 B2 | 4/2019 | Metzmaker et al. |
| 10,272,196 B2 | 4/2019 | Smith et al. |
| 10,279,110 B2 | 5/2019 | Mann et al. |
| 10,300,264 B2 | 5/2019 | Halili et al. |
| 10,307,536 B2 | 6/2019 | Causey et al. |
| 10,322,227 B2 | 6/2019 | Piehl et al. |
| 10,363,365 B2 | 7/2019 | Bazargan |
| 10,376,631 B2 | 8/2019 | Tieck et al. |
| 10,376,632 B2 | 8/2019 | Tieck et al. |
| 10,384,013 B2 | 8/2019 | Krusell et al. |
| 10,391,257 B2 | 8/2019 | Piehl et al. |
| 10,478,554 B2 | 11/2019 | Bazargan et al. |
| 10,517,892 B2 | 12/2019 | Chattaraj et al. |
| 10,532,156 B2 | 1/2020 | Istoc |
| 10,552,580 B2 | 2/2020 | Bazargan |
| 10,603,431 B2 | 3/2020 | Mernoe et al. |
| 10,772,796 B2 | 9/2020 | Kavazov |
| 10,850,032 B2 | 12/2020 | Steck et al. |
| 10,857,287 B2 | 12/2020 | Damiano et al. |
| 10,861,591 B2 | 12/2020 | Grosman et al. |
| 10,960,136 B2 | 3/2021 | Palerm et al. |
| 2002/0038392 A1 | 3/2002 | De La Huerga |
| 2002/0055711 A1 | 5/2002 | Lavi et al. |
| 2002/0065484 A1 | 5/2002 | Douglas et al. |
| 2002/0161332 A1 | 10/2002 | Ramey |
| 2003/0009133 A1 | 1/2003 | Ramey |
| 2005/0015056 A1 | 1/2005 | Duchon et al. |
| 2005/0020980 A1 | 1/2005 | Inoue |
| 2005/0038387 A1 | 2/2005 | Kriesel |
| 2005/0051580 A1 | 3/2005 | Ramey |
| 2005/0154434 A1 | 7/2005 | Simon et al. |
| 2006/0264908 A1 | 11/2006 | Ishii et al. |
| 2007/0088271 A1 | 4/2007 | Richards |
| 2007/0142786 A1 | 6/2007 | Lampropoulos |
| 2007/0161955 A1 | 7/2007 | Bynum et al. |
| 2007/0273671 A1 | 11/2007 | Zadesky et al. |
| 2007/0282294 A1 | 12/2007 | Sidler |
| 2008/0051719 A1 | 2/2008 | Moberg |
| 2008/0188813 A1 | 8/2008 | Miller et al. |
| 2008/0243085 A1 | 10/2008 | DeStefano |
| 2008/0262425 A1 | 10/2008 | Mogensen |
| 2008/0319383 A1 | 12/2008 | Byland |
| 2009/0326506 A1 | 12/2009 | Hasegawa et al. |
| 2010/0049144 A1 | 2/2010 | McConnell et al. |
| 2010/0191165 A1 | 7/2010 | Appling |
| 2010/0217241 A1 | 8/2010 | Mann et al. |
| 2011/0021905 A1 | 1/2011 | Patrick et al. |
| 2011/0118659 A1 | 5/2011 | Maaskamp |
| 2011/0230838 A1 | 9/2011 | Adams et al. |
| 2011/0288494 A1 | 11/2011 | Mendels |
| 2012/0078185 A1 | 3/2012 | Smith |
| 2012/0078197 A1 | 5/2012 | O'Connor et al. |
| 2012/0211946 A1 | 8/2012 | Halili et al. |
| 2012/0211947 A1 | 8/2012 | Halili et al. |
| 2012/0215177 A1 | 8/2012 | Halili et al. |
| 2012/0215178 A1 | 8/2012 | Halili et al. |
| 2012/0215179 A1 | 8/2012 | Halili et al. |
| 2012/0215180 A1 | 8/2012 | Halili et al. |
| 2012/0215183 A1 | 8/2012 | Halili et al. |
| 2012/0226234 A1 | 9/2012 | Bazargan et al. |
| 2013/0046253 A1 | 2/2013 | Yavorsky et al. |
| 2013/0085470 A1 | 4/2013 | O'Connor et al. |
| 2013/0245604 A1 | 9/2013 | Kouyoumjian et al. |
| 2013/0345641 A1 | 12/2013 | German |
| 2015/0057615 A1 | 2/2015 | Mernoe et al. |
| 2015/0073384 A1 | 3/2015 | Limaye |
| 2015/0202375 A1 | 7/2015 | Schabbach et al. |
| 2015/0265826 A1 | 9/2015 | Dudley |
| 2015/0314063 A1 | 11/2015 | Nagar et al. |
| 2015/0357683 A1* | 12/2015 | Lohr .................. H02J 50/10 |
| | | 320/108 |
| 2016/0015885 A1 | 1/2016 | Pananen et al. |
| 2016/0015886 A1 | 1/2016 | Pananen et al. |
| 2016/0015887 A1 | 1/2016 | Pananen et al. |
| 2016/0015911 A1 | 1/2016 | Bazargan et al. |
| 2016/0051760 A1 | 2/2016 | Krusell et al. |
| 2016/0058668 A1 | 3/2016 | Metzmaker et al. |
| 2016/0074587 A1 | 3/2016 | Searle et al. |
| 2016/0082182 A1 | 3/2016 | Gregory et al. |
| 2016/0089493 A1 | 3/2016 | Crouther et al. |
| 2016/0106919 A1 | 4/2016 | Hayter et al. |
| 2016/0184519 A1 | 6/2016 | Blundred et al. |
| 2016/0220754 A1 | 8/2016 | Shaanan et al. |
| 2016/0235910 A1 | 8/2016 | Damiano et al. |
| 2016/0263324 A1 | 9/2016 | Shaanan et al. |
| 2016/0271322 A1 | 9/2016 | Ramey |
| 2016/0361494 A1 | 12/2016 | Jurg et al. |
| 2017/0056590 A1 | 3/2017 | DiPerna |
| 2017/0065768 A1 | 3/2017 | Moore |
| 2017/0182307 A1 | 6/2017 | Halili et al. |
| 2017/0189666 A1 | 7/2017 | Sealfon et al. |
| 2017/0192506 A1 | 7/2017 | Andersen et al. |
| 2017/0216523 A1 | 8/2017 | Neftel et al. |
| 2017/0235920 A1 | 8/2017 | Bauss et al. |
| 2017/0239422 A1 | 8/2017 | Kodgule et al. |
| 2017/0286638 A1 | 10/2017 | Searle et al. |
| 2017/0312454 A1 | 11/2017 | Chattaraj et al. |
| 2018/0036475 A1 | 2/2018 | Lin |
| 2018/0043104 A1 | 2/2018 | Mueller-Pathle |
| 2018/0043105 A1 | 2/2018 | Nazzaro et al. |
| 2018/0103897 A1 | 4/2018 | Amirouche |
| 2018/0104417 A1 | 4/2018 | Nessel et al. |
| 2018/0117248 A1 | 6/2018 | Cabiri et al. |
| 2018/0117296 A1 | 6/2018 | Damiano et al. |
| 2018/0207366 A1 | 7/2018 | Marcoz et al. |
| 2018/0228979 A1 | 8/2018 | Schildt et al. |
| 2018/0280624 A1 | 10/2018 | Bitton et al. |
| 2018/0311435 A1 | 11/2018 | Galasso |
| 2018/0318498 A1 | 11/2018 | Grant et al. |
| 2018/0318506 A1 | 11/2018 | Oakes et al. |
| 2018/0326164 A1 | 11/2018 | Bauss et al. |
| 2018/0353699 A1 | 12/2018 | Helmer et al. |
| 2019/0001060 A1 | 1/2019 | Gylleby et al. |
| 2019/0009032 A1 | 1/2019 | Hautaviita et al. |
| 2019/0015582 A1 | 1/2019 | Naftalovitz et al. |
| 2019/0030247 A1 | 1/2019 | Edwards et al. |
| 2019/0054251 A1 | 2/2019 | Pieronek et al. |
| 2019/0091460 A1 | 3/2019 | Yavorsky et al. |
| 2019/0134305 A1 | 5/2019 | Srinivasan et al. |
| 2019/0151559 A1 | 5/2019 | Byerly et al. |
| 2019/0167900 A1 | 6/2019 | Friedli et al. |
| 2019/0192762 A1 | 6/2019 | Metzmaker et al. |
| 2019/0209775 A1 | 7/2019 | Merchant |
| 2019/0217007 A1 | 7/2019 | Sasaki |
| 2020/0330719 A1* | 10/2020 | Segal .................. A61M 15/008 |
| 2021/0030949 A1 | 2/2021 | Damiano et al. |
| 2021/0030957 A1 | 2/2021 | Damiano et al. |
| 2021/0093777 A1 | 4/2021 | Damiano et al. |
| 2021/0106750 A1 | 4/2021 | Damiano et al. |

FOREIGN PATENT DOCUMENTS

| | | |
|---|---|---|
| JP | 57-124151 | 8/1982 |
| JP | 59-30241 | 2/1984 |
| RU | 2549310 | 4/2015 |
| WO | WO 99/64103 | 12/1999 |
| WO | WO 03/017915 | 3/2003 |
| WO | WO 04/045704 | 6/2004 |
| WO | WO 05/000378 | 1/2005 |

(56) References Cited

FOREIGN PATENT DOCUMENTS

| | | |
|---|---|---|
| WO | WO 05/004973 | 1/2005 |
| WO | WO 06/054367 | 5/2006 |
| WO | WO 09/069511 | 4/2009 |
| WO | WO 07/086186 | 5/2009 |
| WO | WO 09/060741 | 5/2009 |
| WO | WO 11/131778 | 10/2011 |
| WO | WO 12/008285 | 1/2012 |
| WO | WO 12/072555 | 6/2012 |
| WO | WO 12/110474 | 8/2012 |
| WO | WO 12/0115911 | 8/2012 |
| WO | WO 12/146670 | 11/2012 |
| WO | WO 12/160104 | 11/2012 |
| WO | WO 13/161979 | 10/2013 |
| WO | WO 14/104027 | 3/2014 |
| WO | WO 15/061690 | 4/2015 |
| WO | WO 15/061691 | 4/2015 |
| WO | WO 15/061693 | 4/2015 |
| WO | WO 15/155229 | 10/2015 |
| WO | WO 15/166993 | 11/2015 |
| WO | WO 17/007968 | 1/2017 |
| WO | WO 17/199012 | 11/2017 |
| WO | WO 17/217105 | 12/2017 |
| WO | WO 18/129354 | 7/2018 |
| WO | WO 19/021985 | 1/2019 |
| WO | WO 19/046593 | 3/2019 |

OTHER PUBLICATIONS

Ping One Touch Owner's Booklet, Dated Oct. 2014, (360 pages).

Renesas Synergy™ Platform, "Capacitive Touch Hardware Design and Layout Guidelines for Synergy, RX200, and RX100." R01AN3825EU0101 Rev.1.01, Jun. 14, 2017, pp. 1-18.

Boston University, Jan. 2014, Bionic Pancreas: Introducing the iLet 1294 1000, http://sites.bu.edu/bionicpacreas/introducing-the-ilet-1294-1000/, 3 pp.

Brown et al., Apr. 1, 2016, Introducing Beta Bionics: bringing the iLet bionic pancreas to market, https://diatribe.org/introducing-beta-bionics-bringing-ilet-bionic-pancreas-marekt, 3 pp.

Hoskins, Oct. 2, 2018, iLet "Bionic Pancreas" making progress with gen 4 device, Healthline, https//www.healthline.com/diabetesmine/beta-bionics-ilet-update#1, 15 pp.

Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.

Krugman, Aug. 25, 2018, iLet Bionic Pancreas Interface, sarakrugman.com/ilet-interface, 3 pp.

Sifferlin, Apr. 1, 2016, The bionic pancreas is getting closer to reality, time.com, https://time.com/4278068/bionic-pancreas-company, 5 pp.

\* cited by examiner

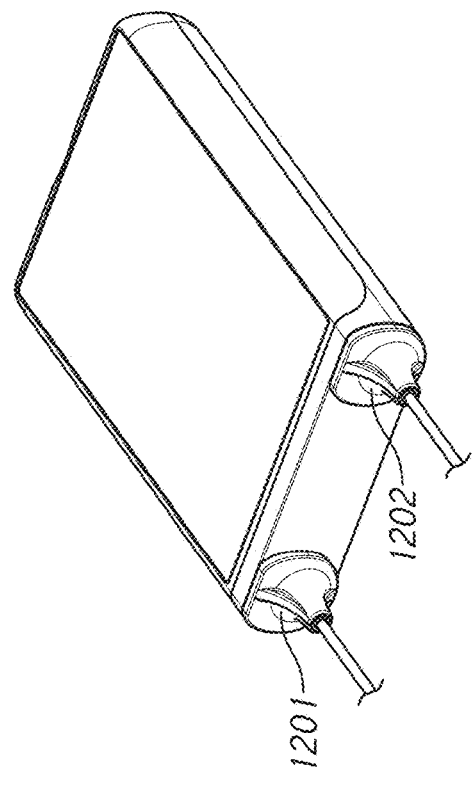
FIG. 1
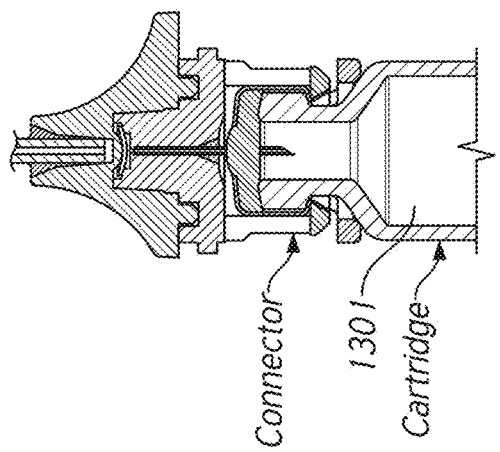
FIG. 2
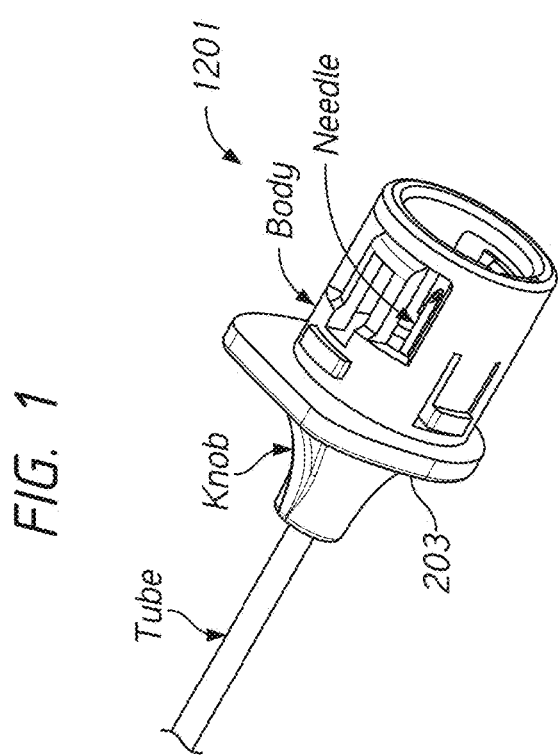
FIG. 3
FIG. 4

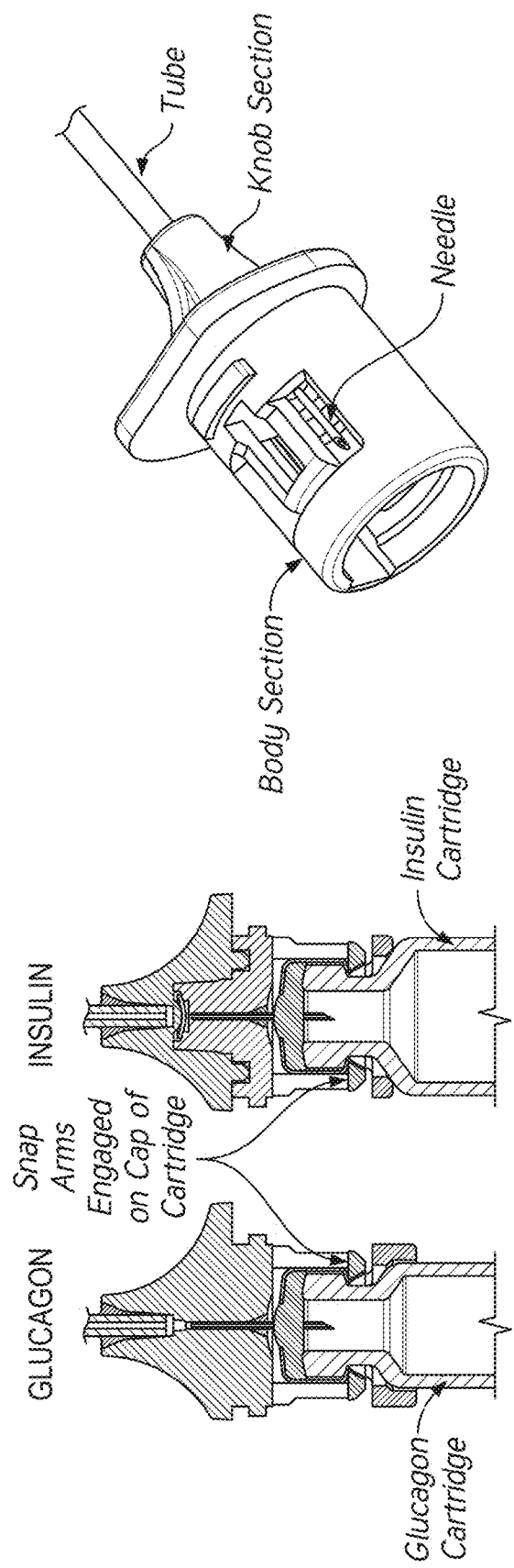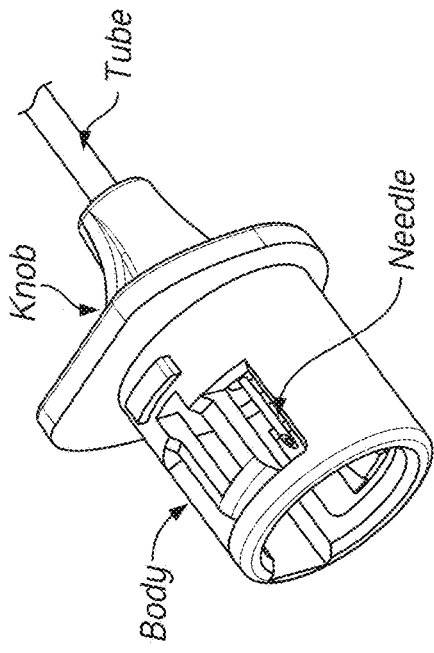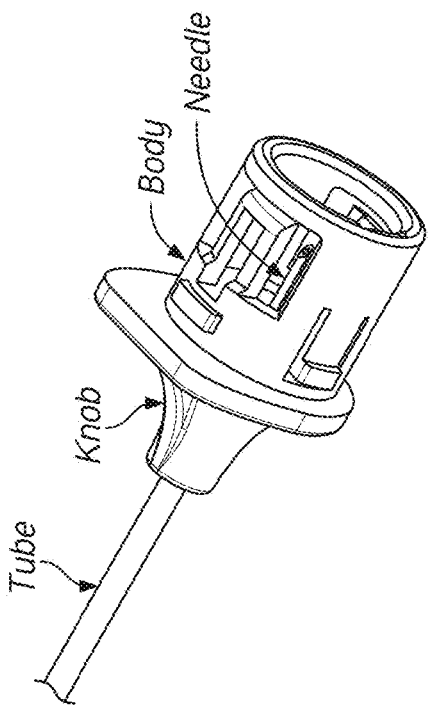

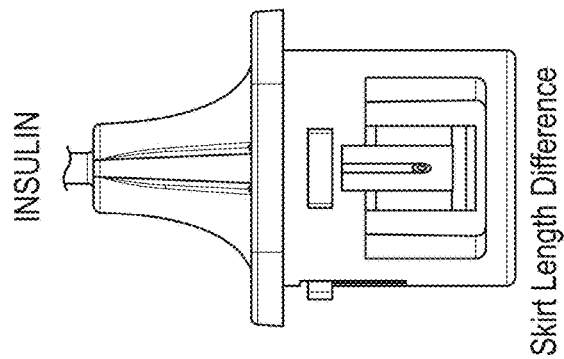
FIG. 26
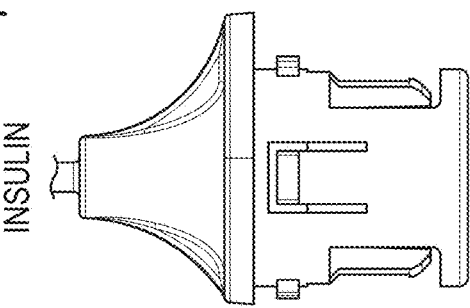
FIG. 27
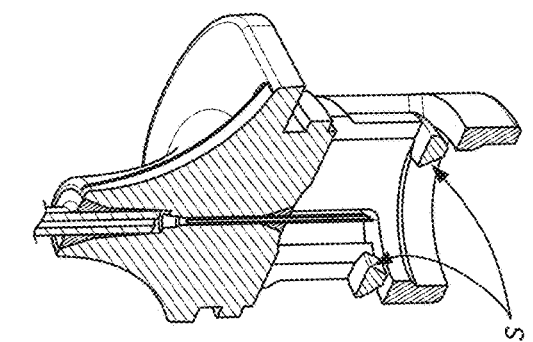
FIG. 25
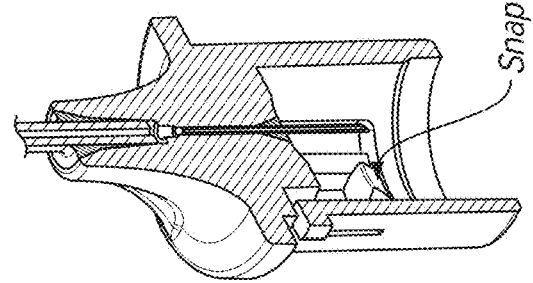

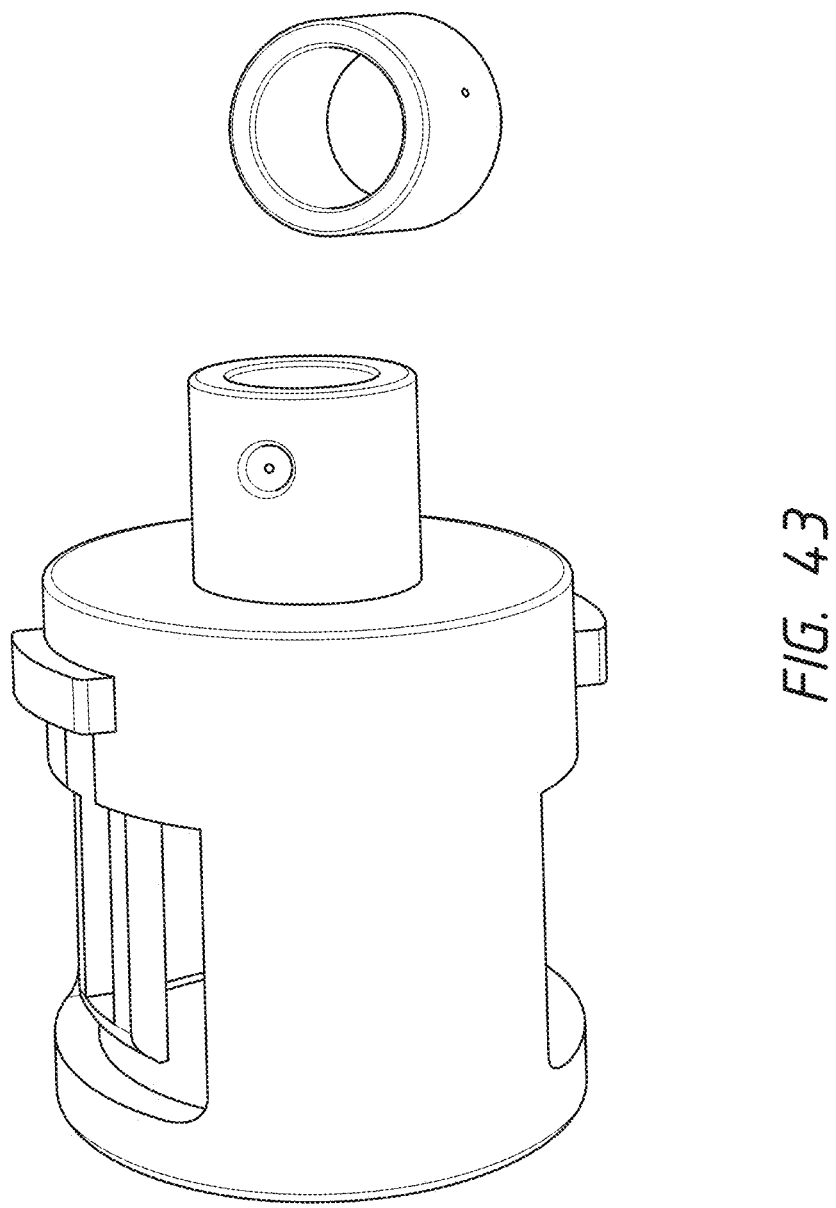

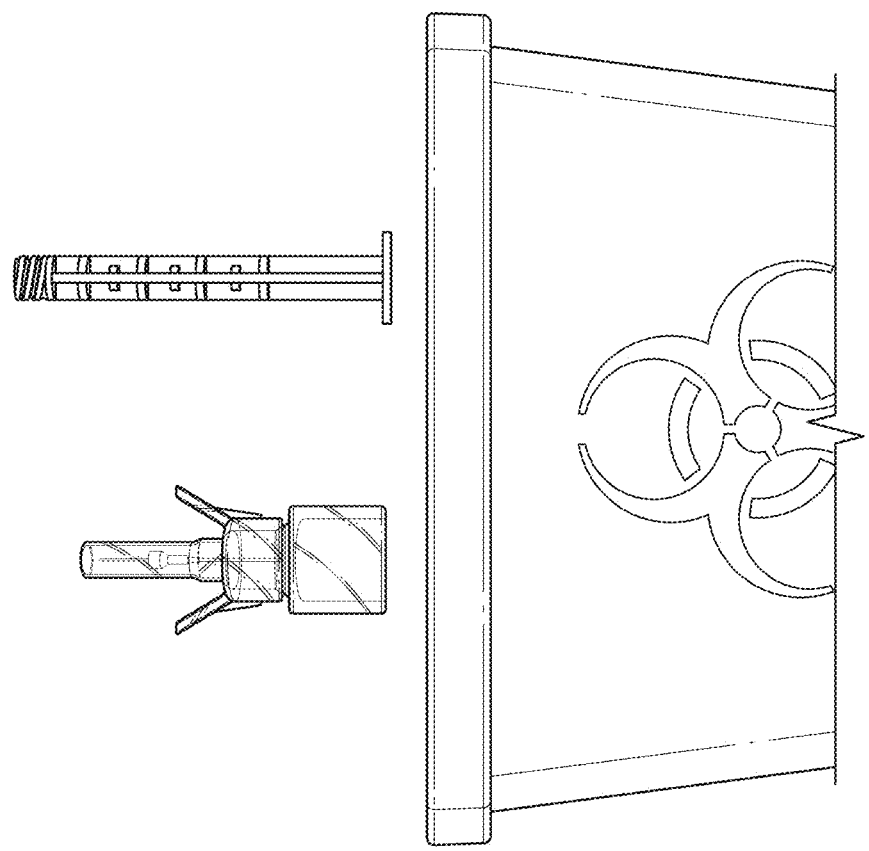
FIG. 68
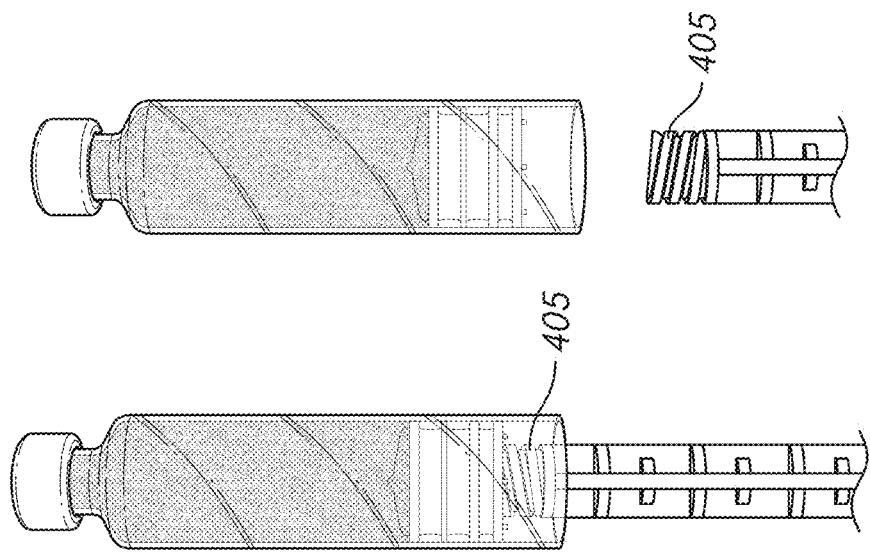
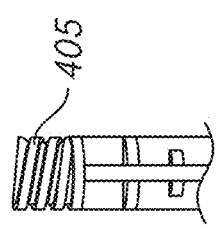
FIG. 67
FIG. 66

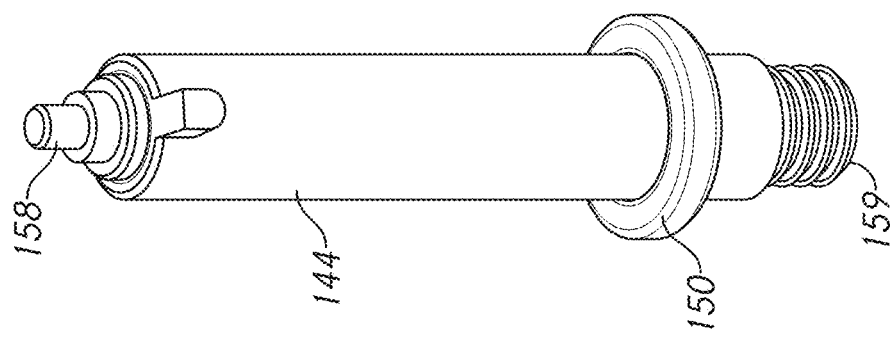
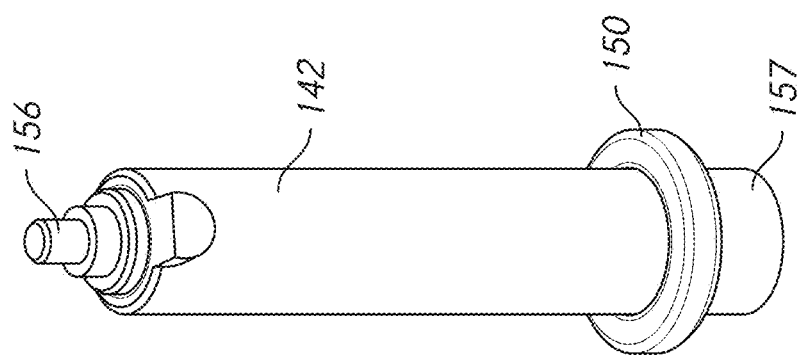
FIG. 73

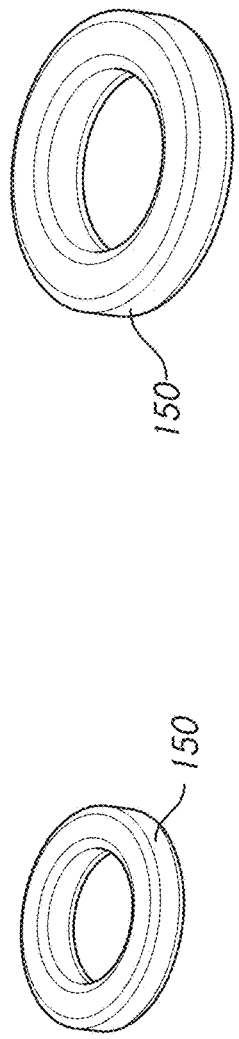
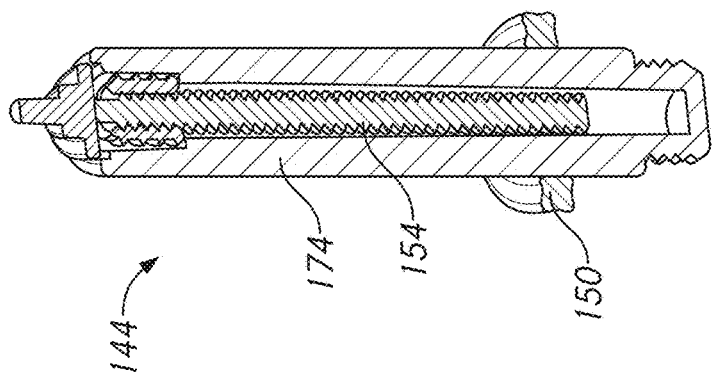
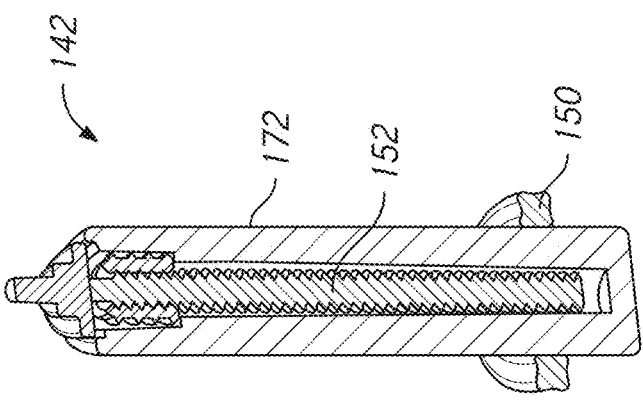
FIG. 74
FIG. 75

INFUSION SYSTEM AND COMPONENTS THEREOF

STATEMENT REGARDING FEDERALLY SPONSORED RESEARCH OR DEVELOPMENT

This invention was made with U.S. Government support under Contract No. DK120234, awarded by the National Institutes of Health. The Government has certain rights in the invention.

COPYRIGHT NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

FIELD

The disclosure relates generally to the field of infusion systems for medicaments and components thereof.

BACKGROUND

For the treatment of certain diseases, including diabetes, medicament pumps can be used to deliver medicines to the patient.

SUMMARY

Sustained delivery, pump driven medicament injection devices generally include a delivery cannula mounted in a subcutaneous manner through the skin of the patient at an infusion site. The pump draws medicine from a reservoir and delivers it to the patient via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a patient while others are configured to deliver multiple medicaments to patient.

A drawback of traditional multi-medicament (e.g., pharmaceutical, hormone, etc.) and certain single medicament regimens is that the patient or physician may accidentally load, transfer, and/or administer the incorrect medicament into the incorrect medicament pump chamber. The accidental administration of the incorrect medicament to the patient can have serious and potentially fatal consequences. For example, standard-of-care insulin therapies for regulating blood glucose in diabetic patients may involve subcutaneous infusion of insulin via an insulin pump. If the amount of dosed insulin is excessive, it can lead to hypoglycemia or a situation of impending hypoglycemia. In some situations, individuals can administer a so-called "rescue dose" of a counter-regulatory agent, such as glucagon. A counter-regulatory agent combats the effect of the excess medicinal dose (e.g., excess insulin) alleviating or substantially preventing adverse effects related to the excess dose.

In a multi-medicament automated system, if the medicaments are accidentally loaded in the incorrect reservoirs or incorrect chambers of a pump, the automated system could deliver an ineffective (and potentially harmful) medicament to the patient. This phenomenon of incorrect medicament administration in automated systems is called cross-channeling. Cross-channeling is dangerous because the wrong medicament could have the opposite of the intended effect or a side effect that is unanticipated. This improper channeling could not only fail to alleviate the patient's condition, but could make the patient's condition worse, or cause a new problem-state for the patient. For example, instead of delivering a rescue dose of a counter-regulatory agent, the delivery system could infuse more and more therapeutic into the patient, exacerbating the issue it was meant to resolve.

Described herein are infusion systems for multiple medicaments (or single medicaments) and various connectors, tubes, cartridges, and pump features that ensure, help ensure, and/or substantially aid in providing proper channeling of each medicament to the patient. Any of the connectors, tubes, cartridges, and pump features used in one embodiments may be mixed and matched to provide systems for lowering the likelihood of mischanneling. Additionally, one or more features disclosed herein may be omitted from an embodiment. While certain embodiments, of infusion systems and components are described below to illustrate various examples that may be employed to achieve one or more desired improvements, these examples are only illustrative and not intended in any way to restrict the general inventions presented and the various aspects and features of these inventions. The phraseology and terminology used herein is for the purpose of description and should not be regarded as limiting. No features, structure, or step disclosed herein is essential or indispensable.

Some embodiments disclosed herein refer to the use of a regulatory agent alone or in combination with a counter-regulatory agent. In some embodiments, where the disease to be treated is diabetes, the regulatory agent is insulin and the counterregulatory agent is glucagon. While diabetic drugs are used as an example elsewhere herein, improper channeling can have deleterious effects in many multi-medicament regimens (e.g., in drugs that regulate pancreatic enzymes, etc.) because a medicament is not administered to the patient at the necessary time or an incorrect medicament is administered at a dangerous level. Thus, the embodiments and considerations provided herein can be applied to any drug individually and/or any drug combination. Additionally, while cross-channeling can refer to systems where two medicaments are inserted into the incorrect chambers of a distribution system, the term cross-channeling as used herein can also refer to systems were more than two medicaments are used and/or where a single medicament is used (for example, when a single medicament is improperly placed in a distribution system).

System Overview

Some embodiments described herein pertain to an infusion system for dosing multiple medicaments (or a single medicament) without cross-channeling. In some embodiments, cross-channeling is avoided by providing design features and/or mating connectors or adapters on certain components of the infusion system. For instance, in some embodiments, the infusion system comprises an infusion pump with one, two, or more infusion chambers (or pump chambers), drive shafts. In some embodiments, the system further comprises cartridges filled with different medicaments, and connectors and tubing that connect to the cartridge to the infusion pump in such a way as to prevent mischanneling or cross-channeling of medicaments. In certain variants, each type of cartridge for each type of medicament has one or more unique differentiating features (either as an integral part of the cartridge or as a component attached or affixed to the cartridge), for example geometric or shape-based features, that allow for unique coupling with a type of connector that itself has unique differentiating features that engage corresponding features in the pump housing and allow for insertion of the proper cartridge into the proper infusion chamber, drive shaft, or pump chamber within the infusion pump.

In certain variants, the system comprises an infusion set. In some embodiments, the infusion set comprises a base with a housing having one or more implements (e.g., delivery members, needles, etc.) that allow delivery medicaments to the patient from the system. In some variants, the housing is connected to a distribution set comprising one or more distribution connectors that are configured to receive a medicament from one or more medicament cartridges (e.g., via a conduit etc.). In some embodiments of the system, one or more fluid conduits provide fluidic communication between the cartridges (e.g., medicament reservoirs) and a distribution connector set. In various implementations, the connector set comprises one or more cartridge connectors that couple the fluid conduits to the medicament reservoirs. In some variants of the system, the cartridge or cartridges is or are located in (and/or can be placed in) a pumping device configured to distribute the medicament from the cartridge or cartridges to the conduit, thereby supplying the system with one or more medicaments. In some embodiments, the fluid conduits provide separate pathways that terminate at designated delivery members (e.g., needles, cannulas, etc.) within the base, thereby enabling independent delivery (e.g., subcutaneous or otherwise) of medicaments separately.

An improved infusion system for multiple medicaments and multiple connectors ensures, helps to ensure, and/or substantially aids in providing proper channeling of each medicament to the patient. In other words, where multiple medicaments are supplied by the infusion systems, the features and/or components described herein are configured to prevent, minimize the occurrence of, or otherwise inhibit the opportunity for a user to inadvertently place a medicament in the incorrect cartridges or to place a cartridge in the incorrect pump chamber. In some embodiments, alternatively, where more than one cartridge is present, both cartridges may comprise a single medicament (e.g., insulin). By providing a system that accommodates two cartridges of the same medicament (and that prevents or inhibits the insertion of cartridges having other medicaments), a user is able to allow the pump to operate for a longer period of time without the need for refilling or adding additional cartridges. Moreover, an expended single cartridge (e.g., one that is empty or close to empty) can be changed on fly by the user without disrupting the flow of medicine from a second cartridge that is providing the medicament to the patient.

BRIEF DESCRIPTION OF THE DRAWINGS

FIGS. 1 and 2 show an embodiment of a multiple medicament pump and one or more cartridge connectors.

FIGS. 3 and 4 show an embodiment of a cartridge connector.

FIGS. 13-37 show embodiments of cartridge connectors.

FIGS. 40-43 show embodiments of a ring valve.

FIGS. 65-67 show embodiments of components for removing a pushrod from a cartridge.

FIG. 68 shows embodiments of components for disposing a pushrod and a transfer hub.

FIG. 73 shows a perspective view of an embodiment of elongate shaft members of an infusion pump.

FIG. 74 shows a perspective view of embodiments of O-rings of an infusion pump.

FIG. 75 shows a cross-sectional view of embodiments of elongate shaft members of an infusion pump.

DETAILED DESCRIPTION

Pump and Cartridge Connectors

An improved embodiment of a multiple medicament pump (including the pump housing) and the one or more cartridge connectors configured to attach to a medicament cartridge is provided in FIGS. 1 and 2. As shown, in some embodiments, the pump 1100 comprises a first medicament chamber 1101 (e.g., insulin) and a second medicament chamber 1102 (e.g., glucagon). Also shown is a pump 1100 engaged with two cartridge connectors 1201, 1202 connected to patient administration tubing lines.

Shown in FIGS. 3 and 4 is an embodiment of a cartridge connector 1201 configured to engage a medicament cartridge 1301 along with a cross-section of the cartridge connector attached to a cartridge. As shown, in some embodiments, the cartridge connector may comprise a knob feature 1203. In some embodiments, the knob is a protrusion or ridge. In some embodiments, the knob allows a user to grip the cartridge connector easily between the finger in the thumb to facilitate placement in the pump chamber and to facilitate locking in the chamber. In some embodiments, the cartridge is locked and/or secured in the pump chamber by providing a quarter turn twist to the knob.

In some embodiments, as shown in FIG. 2, the knob can be of irregular shape (e.g., partially oval with a flat portion, etc.) such that when inserted into the pump, a portion of the knob hangs over the pump to provide a lip that gives tactile feedback that the knob is not correctly positioned and/or is not fully engaged. In some embodiments, when twisted a quarter turn to engage the pump, the knob of the cartridge connector then aligns so that the lip is no longer present and the knob is in alignment with the pump (as shown in FIG. 2).

Figure 5:
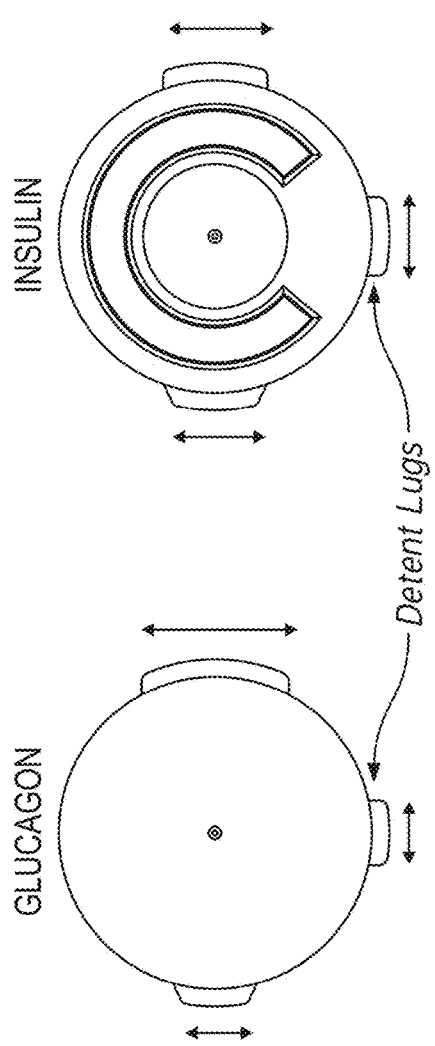
FIG. 5 shows a bottom view of embodiments of cartridge connectors.
Figure 6:
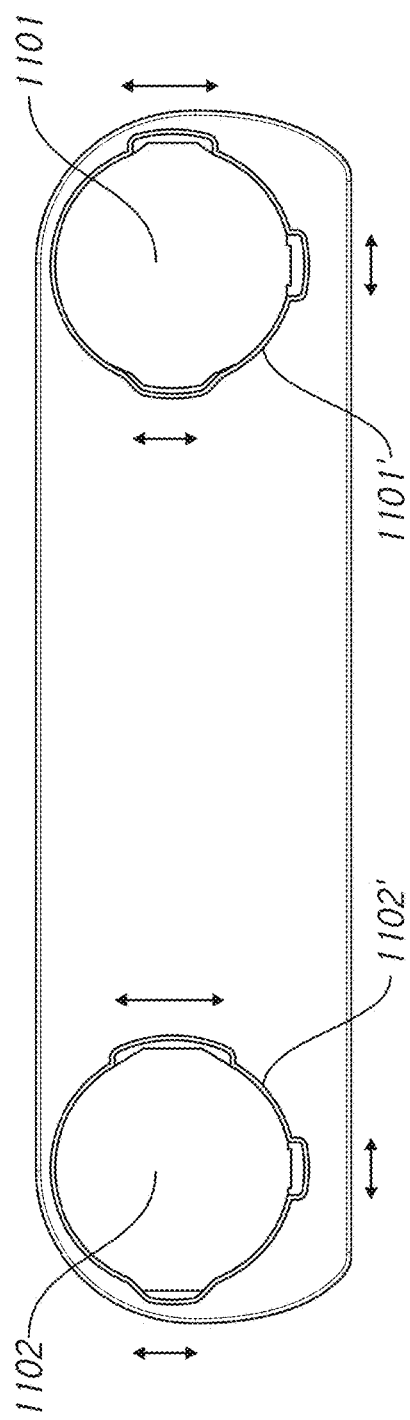
FIG. 6 shows a top view of embodiments of pump chamber openings.

As disclosed elsewhere herein, both the individual cartridge connectors 1201, 1202 and the pump chambers 1101, 1102 may be formed to prevent attachment of the incorrect cartridge connector with the incorrect pump chamber. For example, as illustrated in FIGS. 5 and 6, the glucagon cartridge connector 1202 may be formed to have one or more outwardly protruding lugs of different sizes and/or shapes than the one or more lugs of the insulin cartridge connector 1201, and the openings to the pump chambers 1101', 1102' may also be formed to have detents of varying sizes and/or shapes that correspond to the correct cartridge connector. As such, the different detent sizes and/or shapes of the individual cartridge connectors can prevent insertion and attachment of a cartridge connector with the incorrect pump chamber. FIG. 5 provides a bottom view of individual cartridge connectors showing various lugs. FIG. 6 provides a top view of individual pump chamber openings showing various lug openings to receive corresponding lugs and detents.

Figure 7:
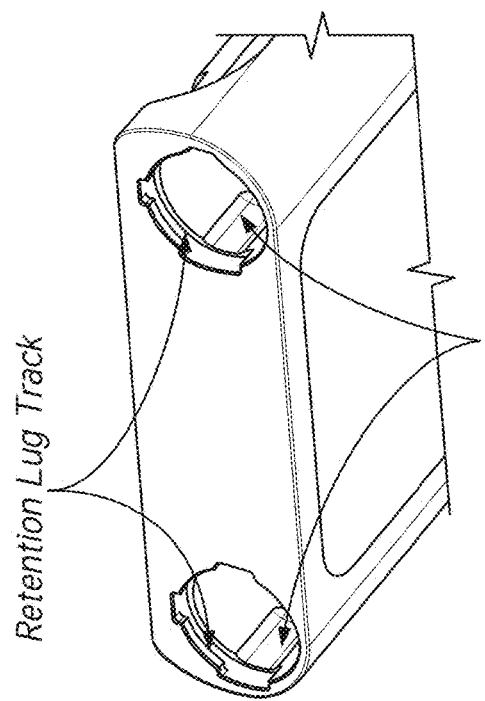
FIG. 7 shows an embodiment of detent cams within pump chambers.
Figure 8:
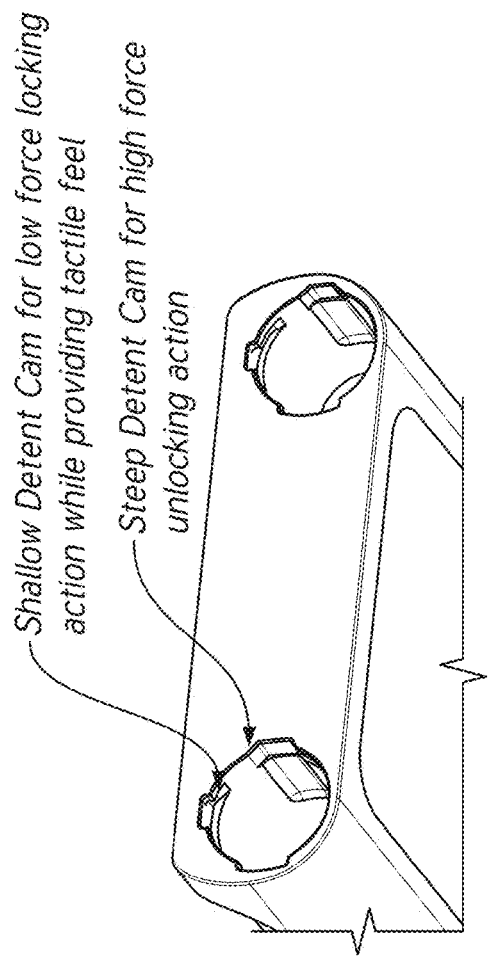
FIG. 8 shows an embodiment of retention lug tracks within pump chambers.

Some embodiments provide for each of the pump chambers having two or more detent cams to facilitate attachment of and prevent disconnection of a cartridge connector from the pump housing. In some embodiments, the pump chamber can include a first "shallow" detent cam that comprises a smaller transition angle than a second "step" detent cam that comprises a larger transition angle. In some embodiments, as the cartridge connector (and corresponding detent lug) is inserted into the opening of the corresponding pump chamber, the cartridge connector is rotated in a first direction to lock the connector into the pump chamber. In some embodiments, while the connector is rotated, one or more of the lugs may abut against and travel along the first "shallow" detent cam until the lug reaches a clearance configured to receive the lug. The clearance may be bordered by the second "steep" detent cam, which would require a greater rotating force in an opposite direction to permit the lug to overcome the second cam and to remove the lug from the clearance. In some embodiments, therefore, the combination of the different detent cams causes cartridge connector to require a greater amount of force to remove the cartridge connector from the pump chamber once it is locked to the pump than the initial amount of force that is required to lock the cartridge connector to the pump chamber. Shown in FIG. 7 is an example of the various detent cams within the pump chambers.

Figure 9:
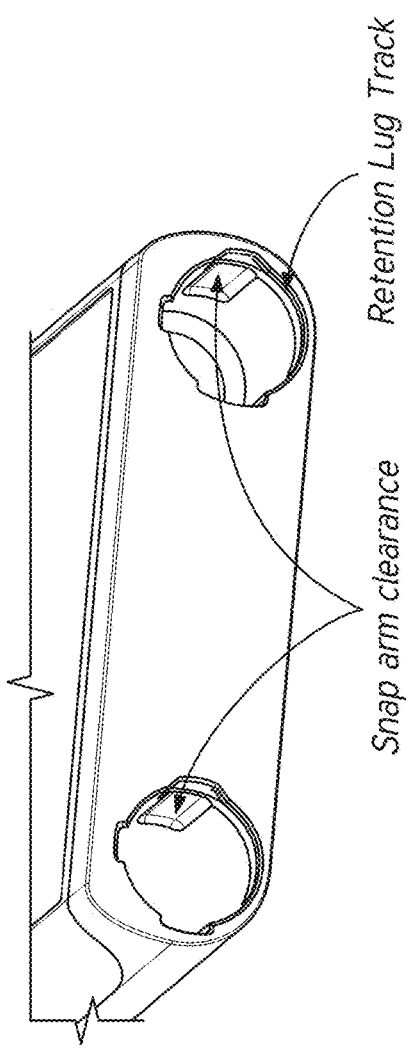
FIG. 9 shows a top view embodiments of pump chamber openings.

As disclosed elsewhere herein, some embodiments provide openings to the pump chambers having various lug opening sizes configured to receive each of the various cartridge connector lugs. Examples are shown in FIGS. 5-9. FIG. 9 provides a top view of the pump chamber openings showing various lug openings to receive corresponding connector lugs.

As described herein, once the cartridge connector is inserted into the pump chamber opening, the connector is rotated to lock the smallest cartridge lug within the lug clearance in the pump chamber. For example, the connector may be rotated a quarter turn to lock to pump chamber. As such, the larger lug of the cartridge connector in initially inserted though the larger lug opening and then is rotated a quarter turn to a position under the smaller lug opening of the pump chamber. The alignment of the larger lug under the smaller opening inhibits removal of the cartridge connector from the pump chamber once locked since the larger lug cannot pass through the smaller lug opening.

Figure 10:
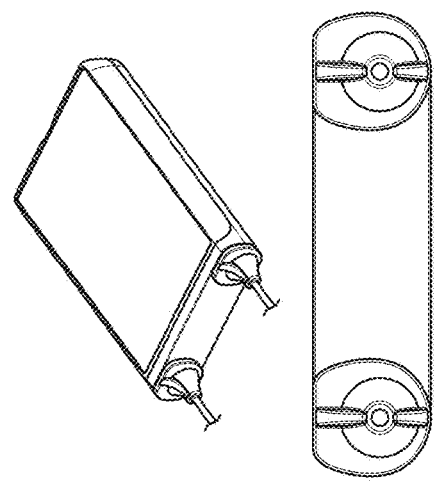
FIGS. 10 and 11 show embodiments of cartridge connectors.
Figure 11:
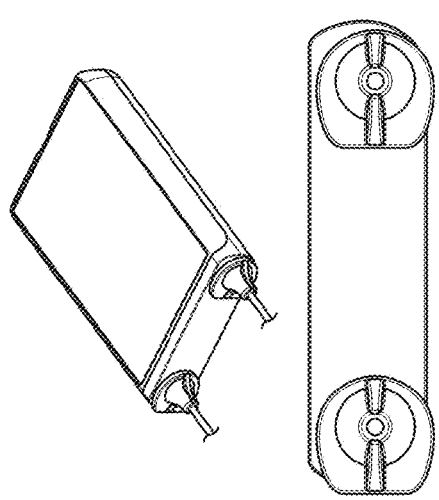

As disclosed elsewhere herein, some embodiments provide for each of the cartridge connectors being shaped so as to provide a visual and/or tactile indication of when the cartridge connector is locked with the pump chamber. For example, in some embodiments, a knob or other physical structure on the cartridge may indicate the orientation of the cartridge and whether the cartridge is in a locked position once the cartridge is inserted into the pump chamber. FIGS. 10 and 11 illustrate an example of the cartridge connector providing a visual indication of when the connector is locked to the pump chamber. FIG. 10 shows cartridges inserted in, but not locked to, the pump chamber. FIG. 11 shows cartridges aligned with pump chamber after quarter turn to indicate locked state.

As shown in FIGS. 10 and 11, the cartridge connectors may be configured to allow clockwise turning to lock the cartridges in place. In other embodiments, not shown, where different medicaments are used, the cartridge connectors and pump openings may be configured to require a clockwise turn to lock one cartridge connector (and cartridge) in place and counter clockwise turning to lock the other cartridge connector (and cartridge) in place. Thus, another indicator that allows a user to avoid mischanneling may be added.

In some embodiments, as disclosed elsewhere herein, the orientation of the "Knob" feature of the Cartridge Connectors may allow insertion with asymmetric alignment and locking with symmetric alignment after clockwise quarter turn (or counter clockwise, or both).

Figure 12:
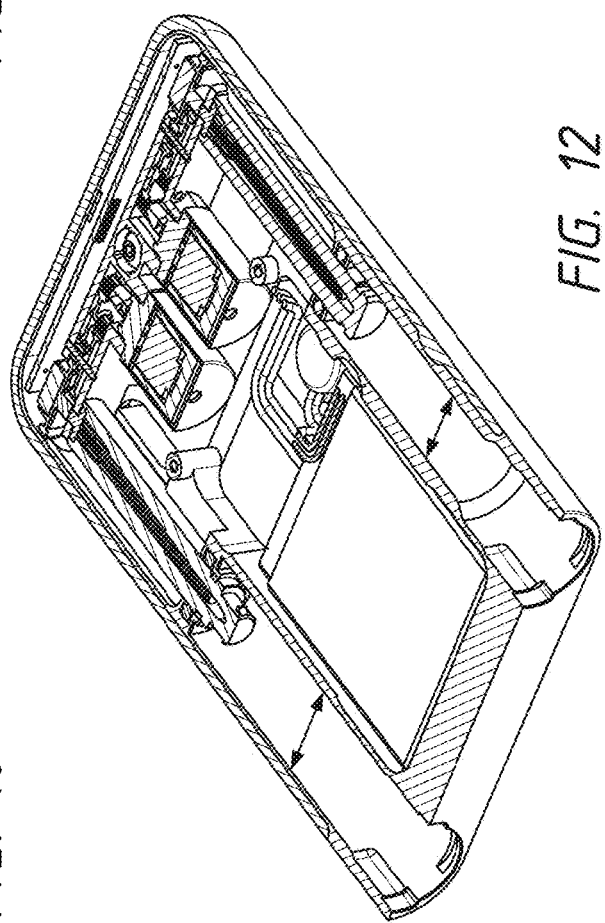
FIG. 12 shows embodiments of pump chambers.

In some embodiments, as disclosed elsewhere herein, the chamber diameters may be different and as shown in FIG. 12. In some embodiments, for example, the insulin cartridge cannot be inserted into glucagon chamber. In some embodiments, the glucagon cartridge (which is smaller diameter) can go into the insulin chamber. In some embodiments, however, a stop rib in the bottom of the chamber prevents full insertion. It will be appreciated that, likewise, the glucagon cartridge may be larger than the insulin chamber to achieve the opposite effect. In some embodiments, the glucagon cartridge includes an insertion stop rib. In some embodiments, the stop rib prevents the glucagon cartridge from seating low enough to allow the connection within the insulin chamber.

In some embodiments, an o-ring is not used in this design at the cartridge connector. In some embodiments, the cartridge connectors are not designed to seal the housing and the housing sealing function is elsewhere. Therefore, the cartridge chambers are permitted to "breath" as required (to avoid runaway dosing upon pressure changes in, for example, an airplane).

Cartridge Connectors

In some embodiments, both the individual cartridge connector shrouds and the individual medicament cartridges may be formed to prevent attachment of the incorrect cartridge connector with the incorrect medicament cartridge. For example, as illustrated in FIG. 13, the glucagon cartridge connector may be formed to have a longer shroud (e.g., skirt) than the insulin cartridge connector, and the insulin cartridge may be formed to have a wider diameter than the glucagon cartridge. As such, the longer shroud of the glucagon cartridge connector would abut against a larger diameter vial of the insulin medicament cartridge; thus, preventing the snap arms and needle cannula of the glucagon cartridge connector from engaging and connecting to the insulin cartridge.

In other embodiments, the shroud of the insulin cartridge is longer to avoid engaging a glucagon cartridge that may be wider than the insulin cartridge.

In some embodiments, as shown in FIG. 14, additional features may include one or more of a needle that is recessed within the connector above the shroud and a skirt that forms an uninterrupted ring around the bottom of the cartridge connector. In some embodiments, these features prevent the vial from being pressed into the connector and/or may prevent improper puncture of the vial septum.

In some embodiments, as disclosed elsewhere herein, the connector set comprises one or more cartridge connectors that couple the fluid conduits (shown in FIG. 15) to the medicament reservoirs. In some variants of the system, as disclosed elsewhere herein, the reservoirs (or reservoir) are located in (and/or can be placed in) a pumping device configured to distribute the medicament from the reservoirs (or reservoir) to the conduit, thereby supplying the system with medicaments. In some embodiments, the fluid conduits provide separate pathways that terminate at designated delivery members (e.g., needles, cannulas, etc.) within the base, thereby enabling independent delivery (e.g., subcutaneous or otherwise) of medicaments separately.

As shown in FIG. 16, in some embodiments, there are a one or more snap arms (e.g., 1, 2, 3, 4, or more) molded into the body of the cartridge connector. In some embodiments, these arms "snap" onto the "cap" of the drug cartridge when the cartridge connector is attached. In some embodiments, these snap arms are in a position that ensures the cartridge is extracted from the pump when the cartridge connector is disconnected. In some embodiments, without this connection, the cartridge could be stuck in the pump by the forces on the Plunger/Pump connection.

Figure 17:
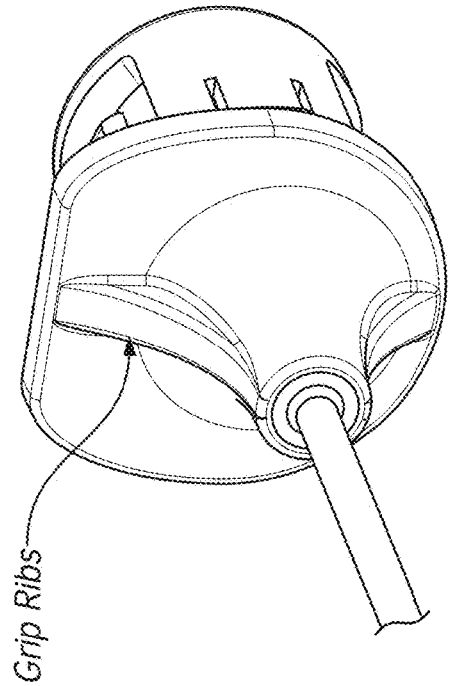

FIG. 17 provides a view of a cartridge connector skirt ring, which may be provide on the cartridge connector. In some embodiments, the "skirt ring" ensures that the cartridge connector is perpendicular to the cartridge before the needle penetrates the cartridge seal. In some embodiments, non-perpendicular needle penetration has been shown to cause leakage at the seal.

Figure 18:
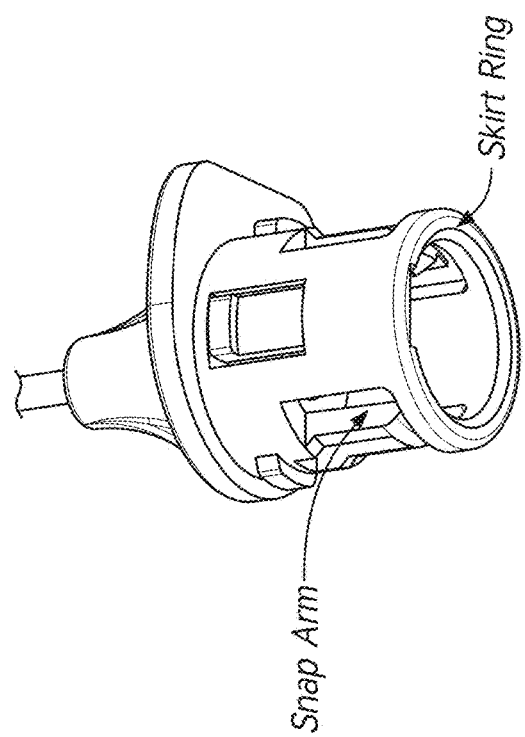

In some embodiments, "grip ribs", as shown in FIG. 18, help the user develop the torque needed to connect the cartridge connector to the pump. In some embodiments, as disclosed elsewhere herein, the connection is made by rotating the cartridge connector a quarter turn. In some embodiments, a detent is provided to give tactile feedback when the connection is made. In some embodiments, a shallow cam for the detent as it rotates into the connected position keeps the connection forces low. In some embodiments, a steep cam for the detent is used to cause the disconnect forces to be higher that the connection forces. This is intended to minimize inadvertent disconnection.

Figure 19:
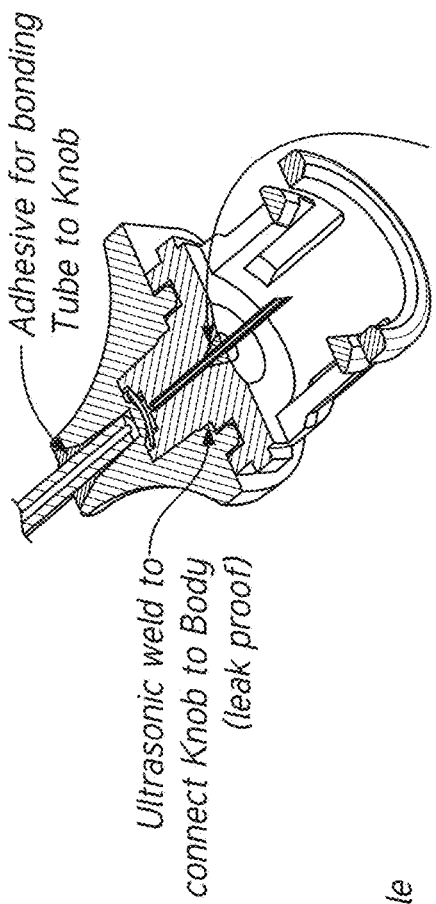
Figure 20:
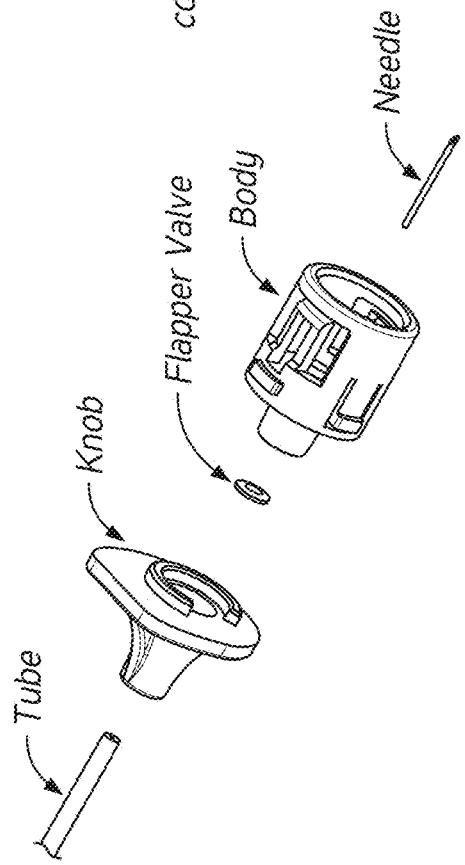
Figure 21:
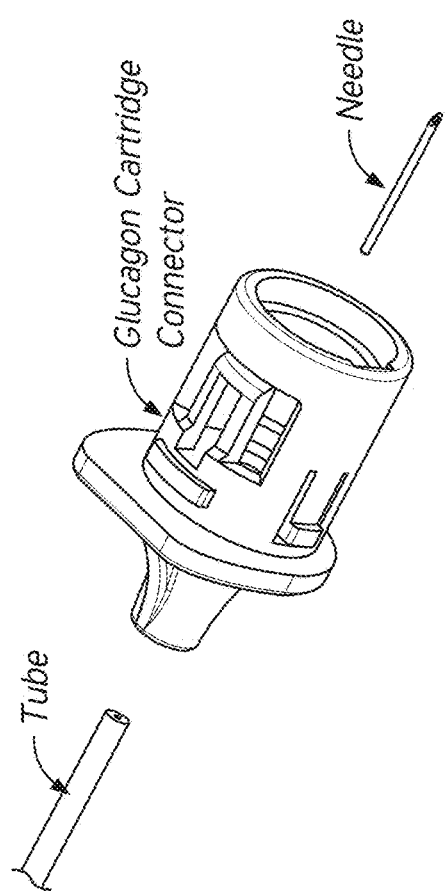
Figure 22:
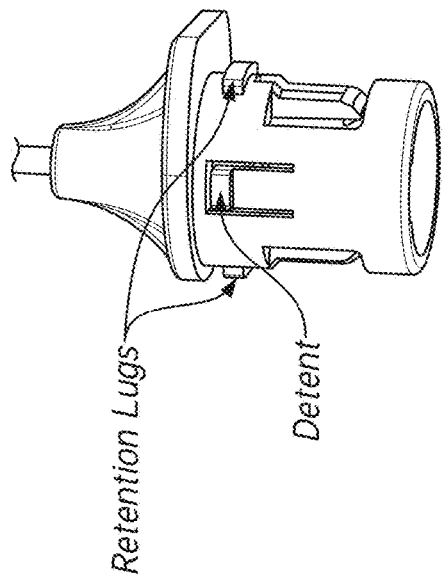
Figure 23:
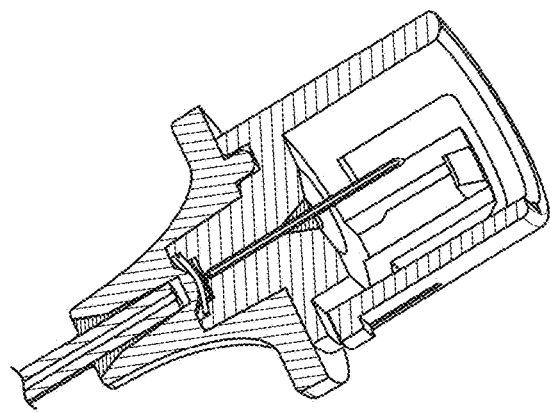

Some embodiments pertain to methods of making a cartridge connector. In some embodiments, as shown in FIG. 19, the cartridge connector is made by employing one or more of the following steps: a needle is bonded to the body; a tube is bonded to the knob; a check valve (e.g., a flapper valve) is set onto the "Valve Seat" of the body; the knob and body are sonically welded together. In some embodiments, as shown in FIGS. 19 and 20, the tube mounting hole in the knob may be tapered so that the tube will contact the wall around the perimeter before bottoming out in the hole. This creates a seal to prevent adhesive from running down into the check valve area when glueing the tube into the knob In some embodiments, as shown in FIGS. 21-23, the cartridge connector can be made by employing one or more of the following steps: the Needle is bonded to the Body; the Tube is bonded to the Knob.

Figure 24:
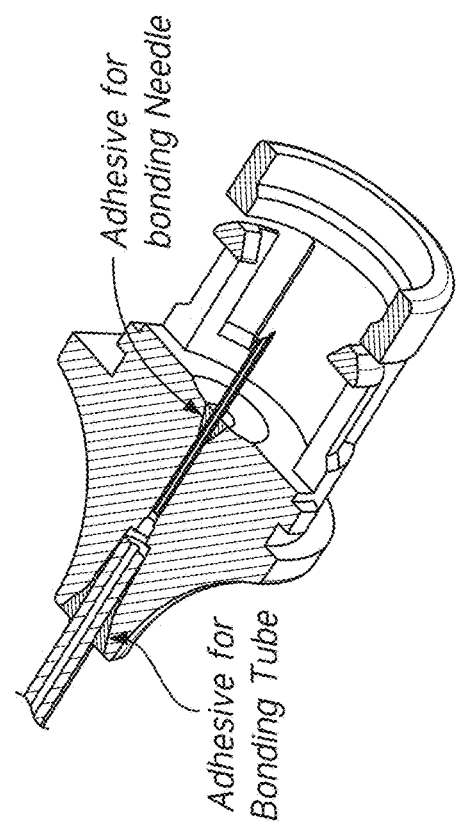

As disclosed elsewhere herein and as shown in FIG. 6, in some embodiments, the retention lug features are used to retain the cartridge connector in the pump. Embodiments of retention lugs and detents are shown in FIG. 24 (and elsewhere herein). In some embodiments, as disclosed elsewhere herein, the size of the retention lugs can be varied to prevent connecting the wrong cartridge connector. For example, one cartridge connector (e.g., the insulin cartridge connector) may have larger or smaller detents and/or larger or smaller detents retention lugs than another cartridge connector (e.g., the glucagon cartridge connector). In some embodiments, lugs and detents may be in different positions on the difference cartridge connectors. In some embodiments, the detent provides increased connection security to prevent inadvertent disconnection.

Figure 29:
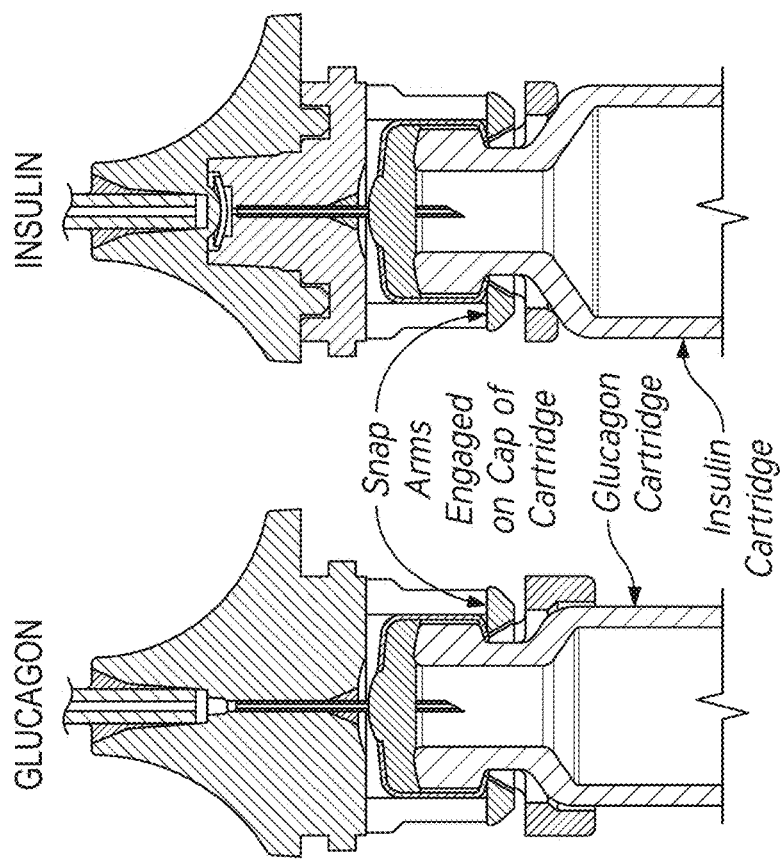
Figure 28:
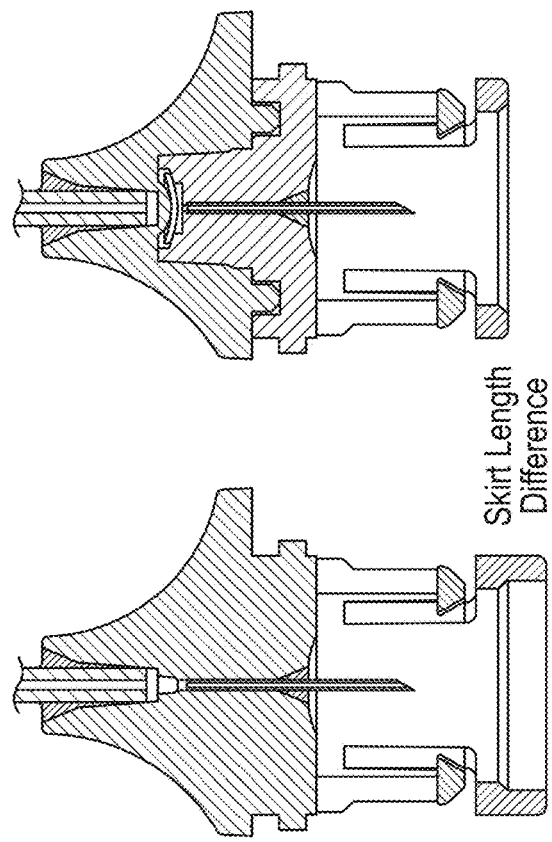
Figure 31:
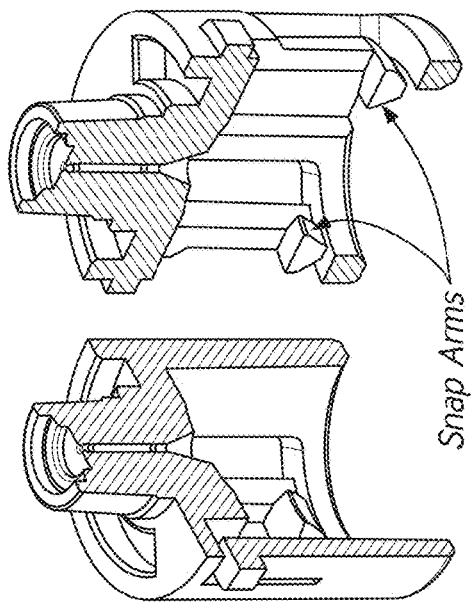
Figure 33:
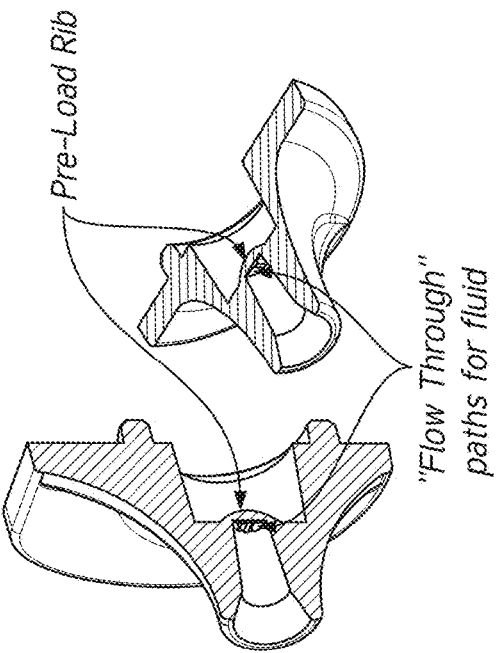
Figure 30:
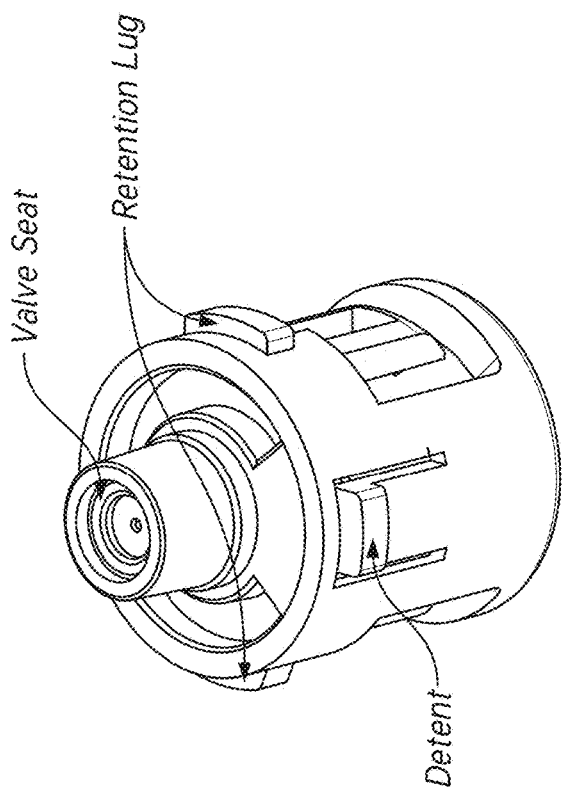
Figure 32:
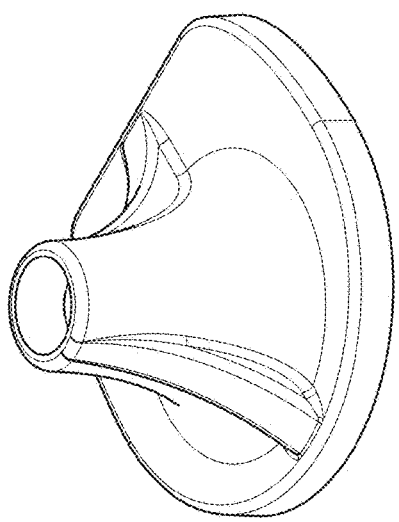
Figure 35:
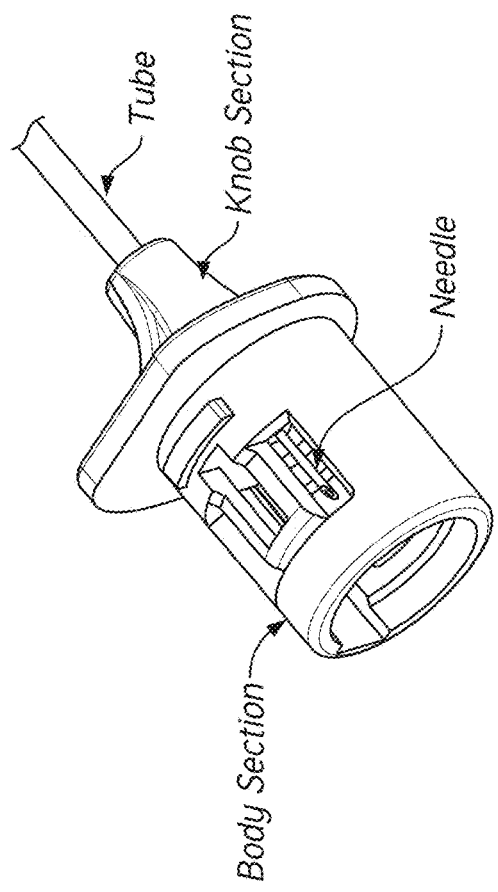
Figure 37:
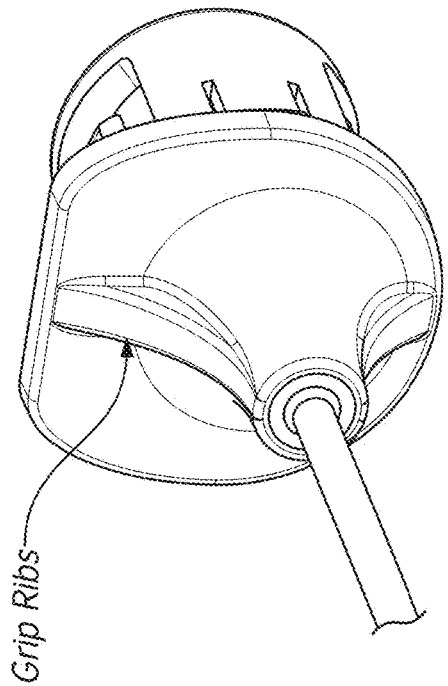
Figure 34:
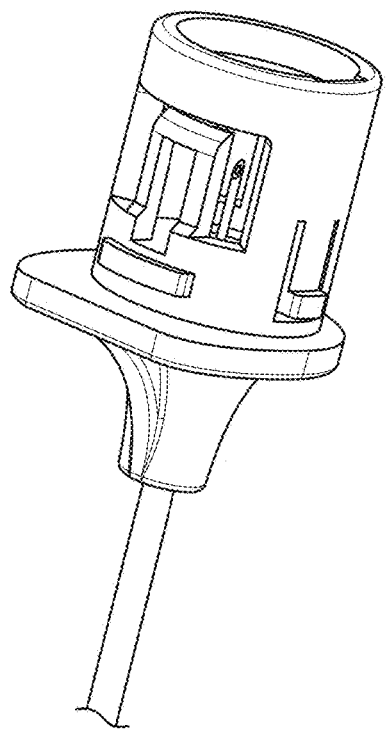
Figure 36:
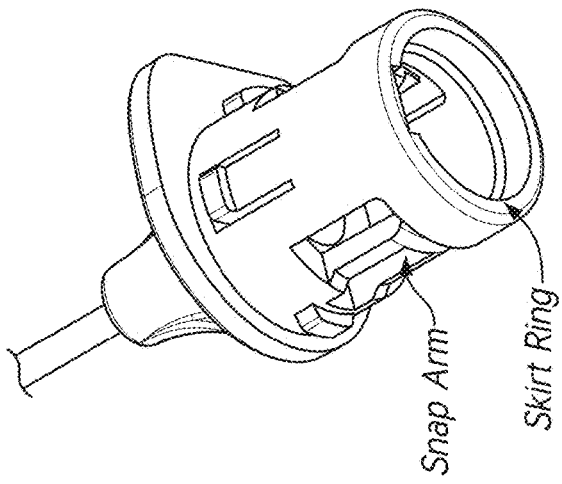

In some embodiments, as disclosed elsewhere herein, the cartridge connectors comprise different length skirts. As shown in FIGS. 26 and 27, the longer skirt of a cartridge connector (e.g., glucagon) will hit a larger diameter cartridge (e.g., insulin) preventing the snap connection of the snap arms. In some embodiments, the cartridge connector cannot rotate into the locked position if the cartridge snaps are not closed. FIGS. 28 and 29 provide some embodiments of optional differences between the two cartridge connectors (e.g., glucagon and insulin). As disclosed elsewhere herein, in some embodiments, the size of the retention lugs can be varied to prevent connecting the wrong cartridge connector. As disclosed elsewhere herein, in some embodiments, the detent may provide increased connection security to prevent inadvertent disconnection.

FIGS. 30-37 provide additional views of cartridge connectors with a variety of features for the prevention or reduction of mischanneling. In some embodiments, as shown, there are two snap arms molded into the body section (see also FIG. 25). In some embodiments, these arms snap onto the cap of the drug cartridge when the cartridge connector is attached. In some embodiments, these snap arms are then in position to ensure the cartridge is extracted from the pump when the cartridge connector is disconnected. In some embodiments, without this connection, the cartridge could be stuck in the pump by the forces on the plunger/pump connection. In some embodiments, the skirt ring ensures that the cartridge connector is perpendicular to the cartridge before the needle penetrates the cartridge seal. Non-perpendicular needle penetration has been shown to cause leakage at the seal. In some embodiments, the grip ribs help the user develop the torque needed to connect the cartridge connector to the pump. In some embodiments, the connection is made by rotating the cartridge connector a quarter turn. In some embodiments, a detent is provided to give tactile feedback when the connection is made. In some embodiments, a shallow cam for the detent as it rotates into the connected position keeps the connection forces low. In some embodiments, a steep cam for the detent is used to cause the disconnect forces to be.

It should be appreciated that any of the features of the cartridge connectors, pumps, and/or cartridges disclosed herein (e.g., retention lugs (shape, size, and position), detents (shape, size, and position), skirts (length and diameter), threading (e.g., different directional, such as clockwise counter clockwise), cartridge connectors (shape, size, and position), coinciding receiving portions on the pump receptacles, etc.) may be used in combination to provide multiple cartridge connectors and pumps that avoid mischanneling. Likewise, one or more of features disclosed herein for the cartridge connectors (e.g., retention lugs and detents) could instead be provided on the pump receptacle and the coinciding pump features described above (lug and detent tracks) could instead be provided on the cartridge connectors. Moreover, as disclosed elsewhere herein, the cartridge connectors, pumps, and/or cartridges disclosed herein could lack one or more features disclosed herein.

Check Valve

Some embodiments, provides for the cartridge connector including a valve along a medicament fluid pathway within the cartridge connector that is configured to prevent unintentional leaking of the medicament from the medicament cartridge and/or retraction of fluid back into the cartridge once expelled. For example, the valve allows fluid to pass only after reaching a threshold pressure (e.g., a crack pressure) within the cartridge. The threshold pressure needed to allow fluid flow passed the valve can be greater than any gravitationally induced hydrostatic pressure differential that might develop between the patient and the infusion system to prevent inadvertent leaking. By way of another example, the valve may comprise a unidirectional valve such that the valve permits fluid flow in one direction (e.g., from the cartridge towards the patient) but inhibits fluid flow through the valve in the opposite direction.

Figure 39:
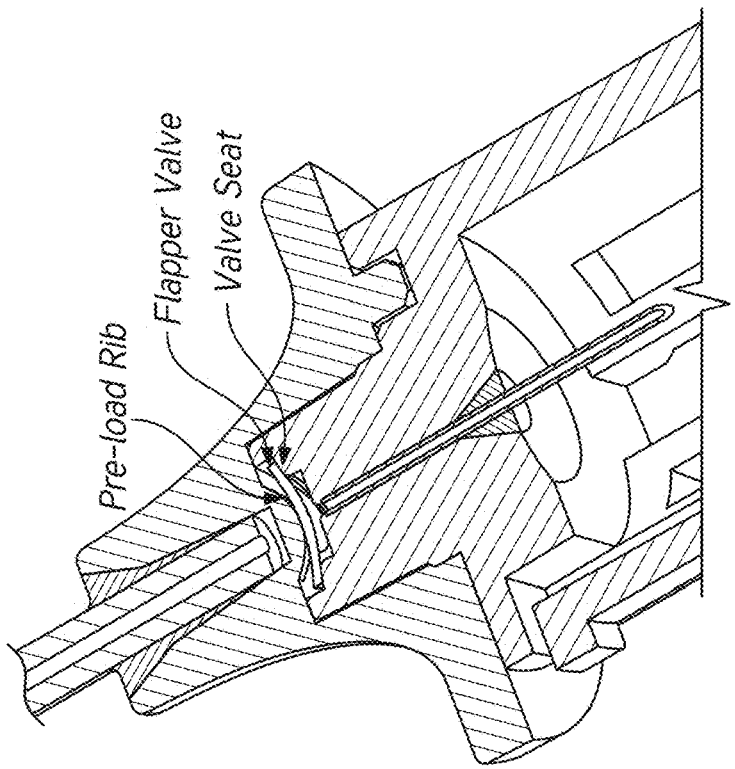
FIGS. 38 and 39 show an embodiment of a valve within a cartridge connector.
Figure 38:
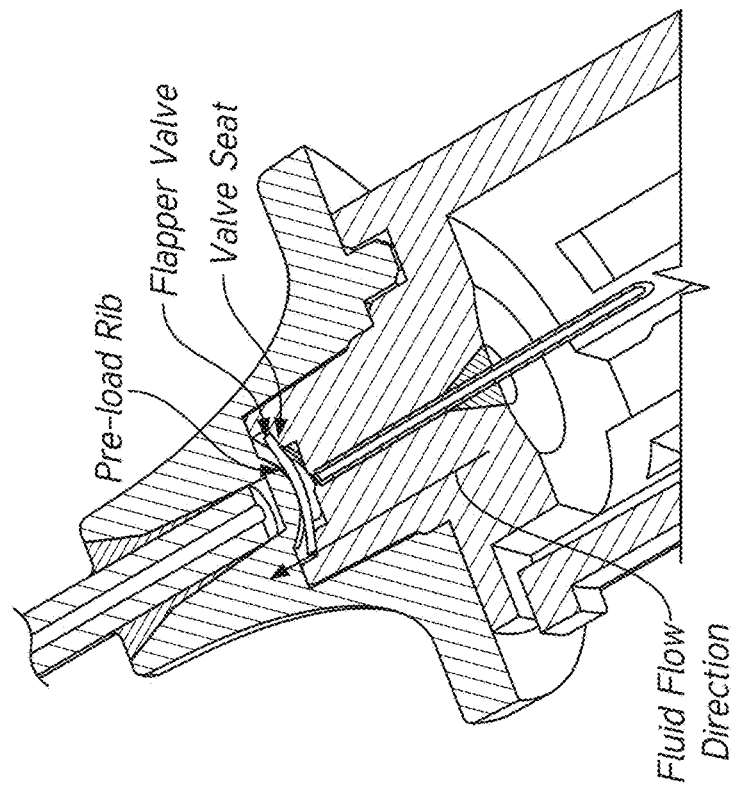
Figure 40:
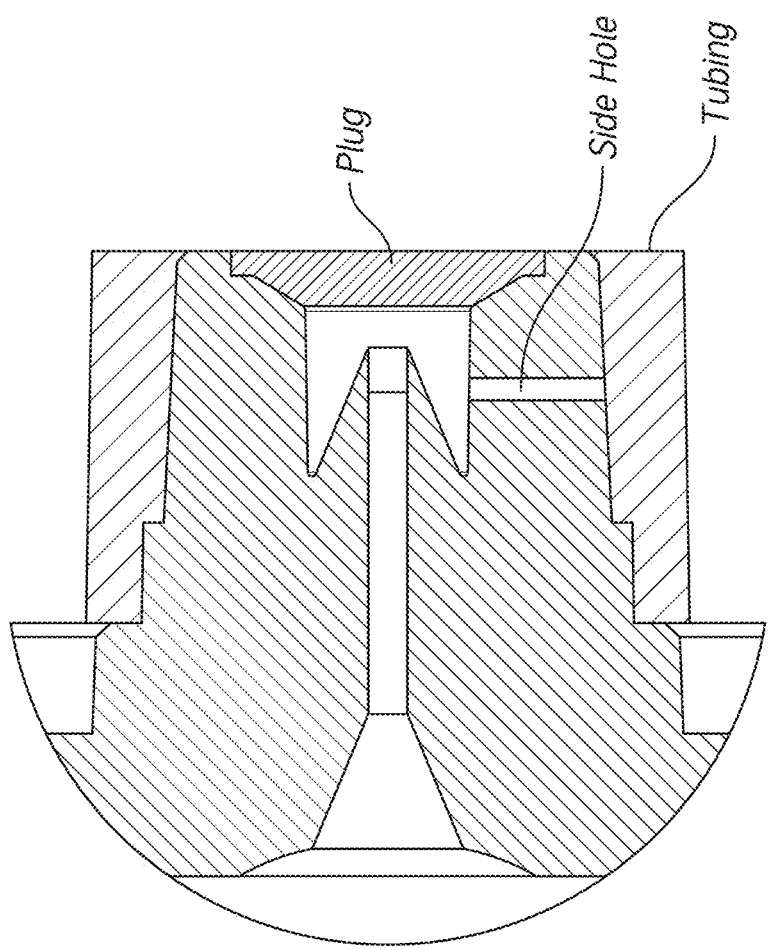
Figure 41:
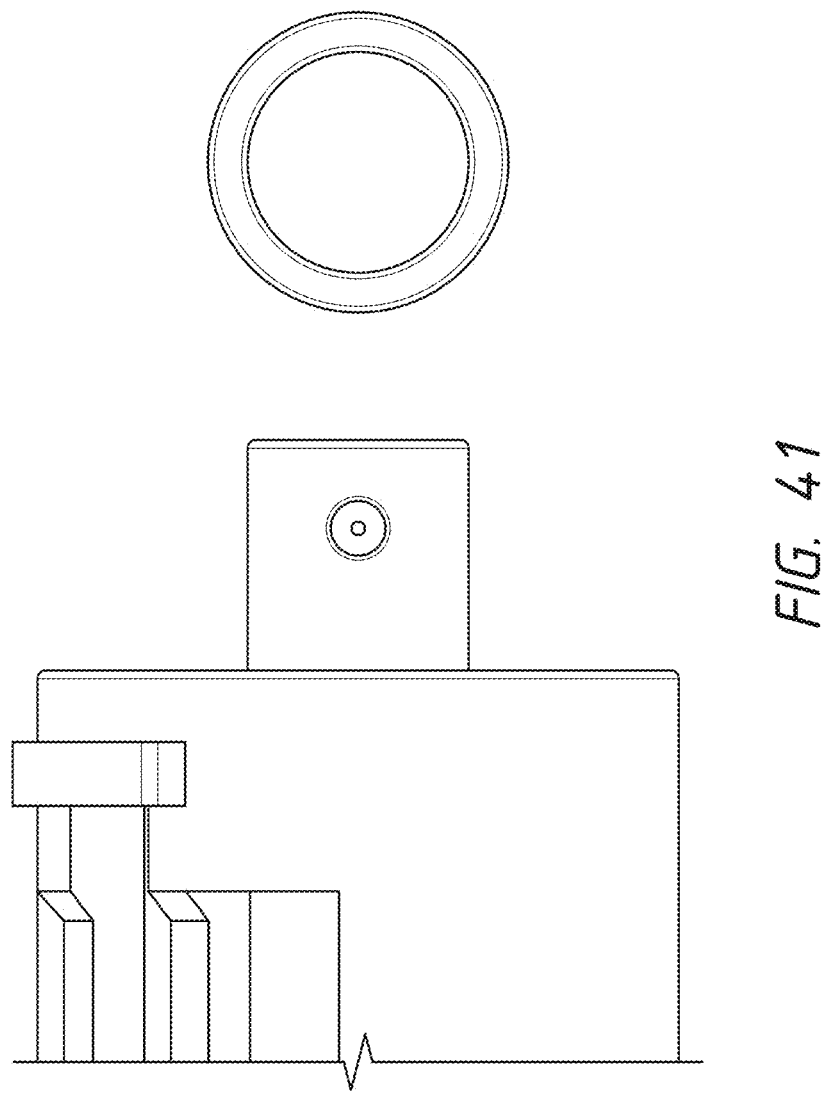
Figure 42:
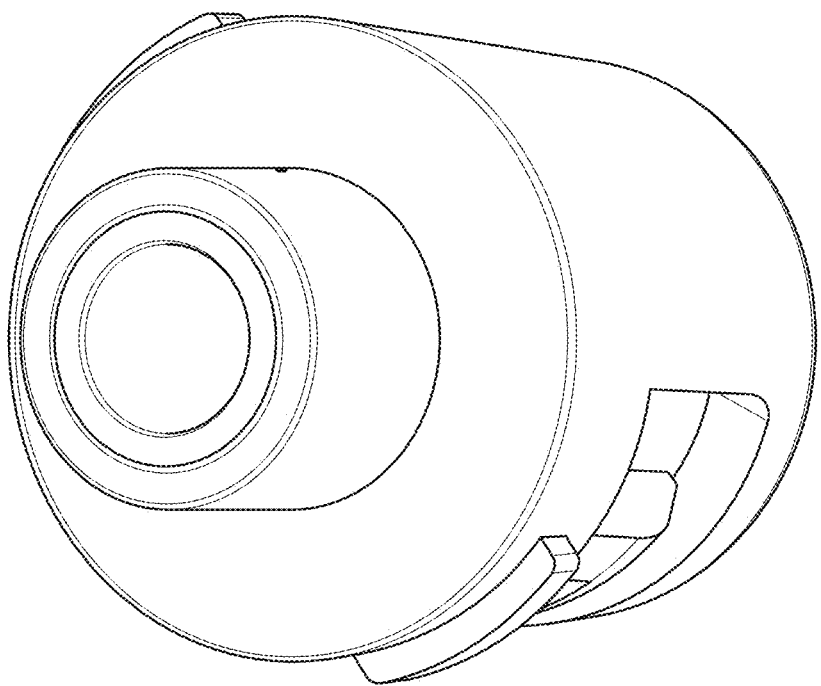
Figure 45:
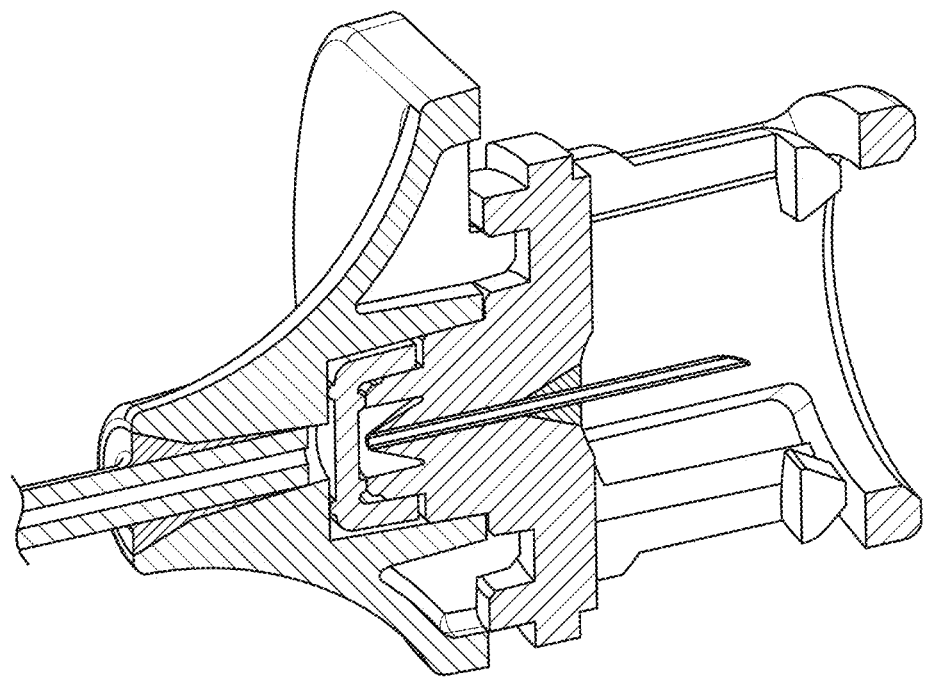
FIGS. 44-47 show an embodiment of a cartridge connector with a check valve.
Figure 44:
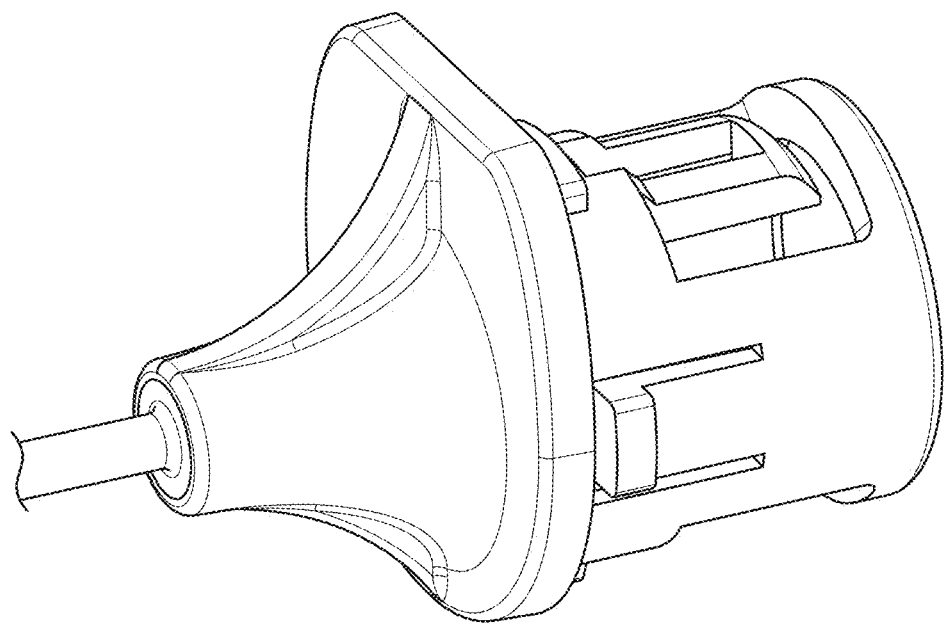
Figure 47:
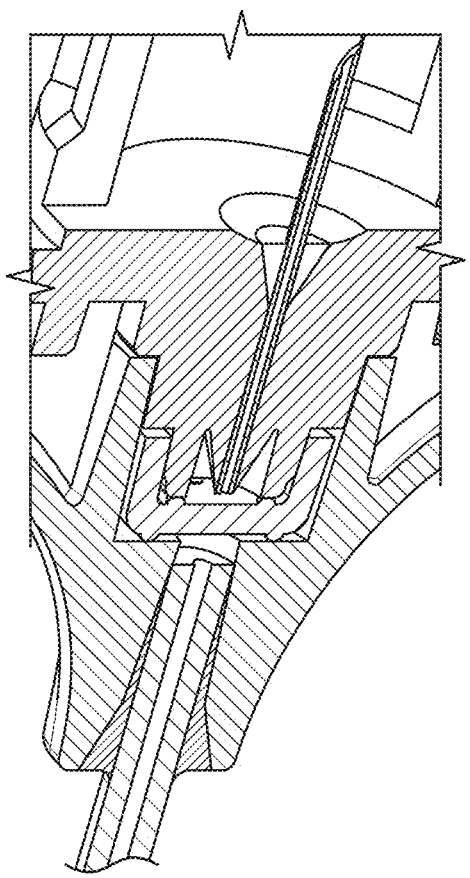
Figure 46:
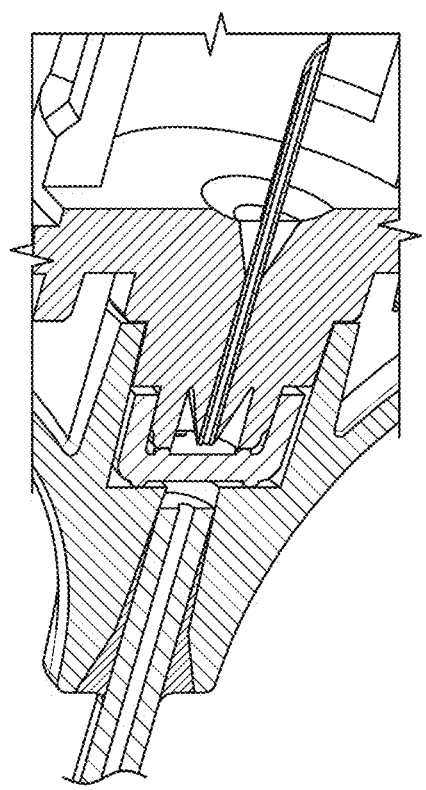
Figure 49:
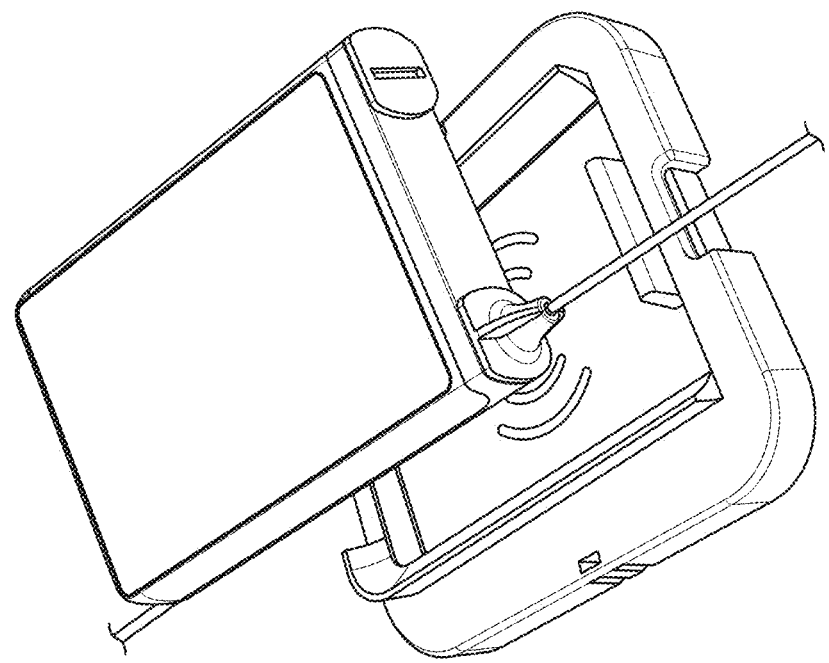
FIGS. 48-51 show an embodiment of an inductive charging pad and a medicament pump.
Figure 48:
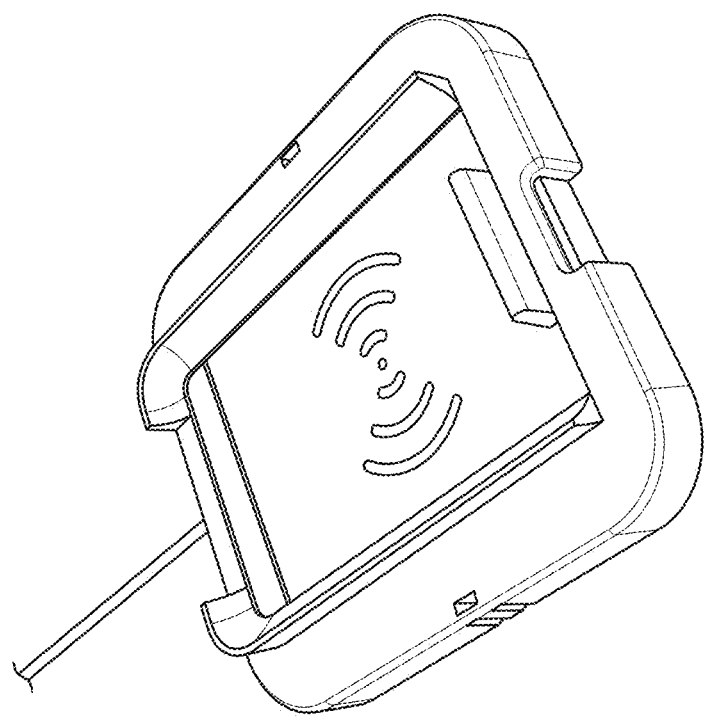
Figure 51:
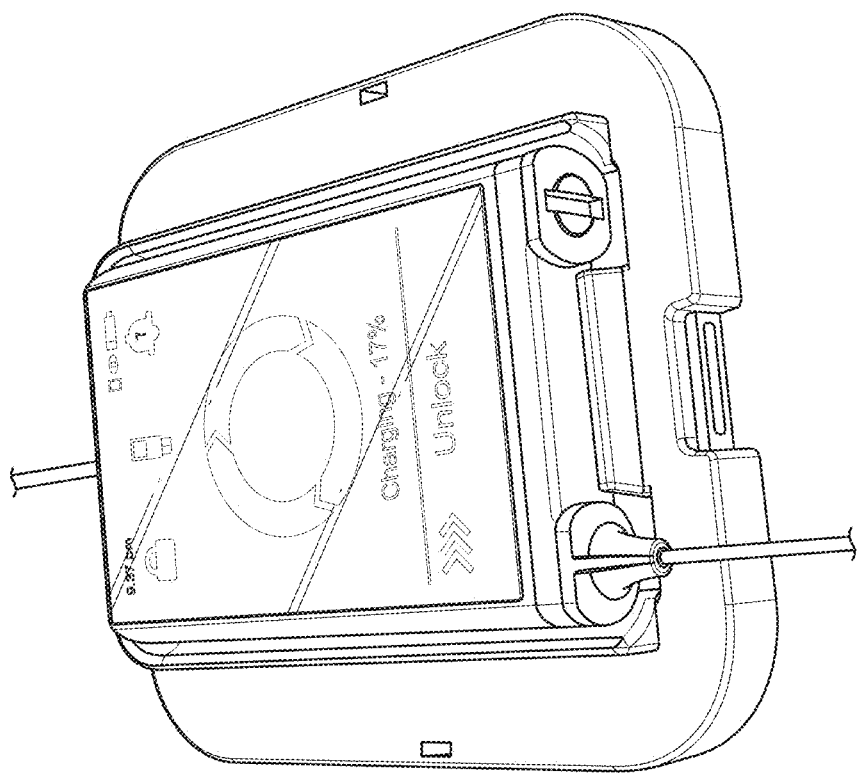
Figure 50:
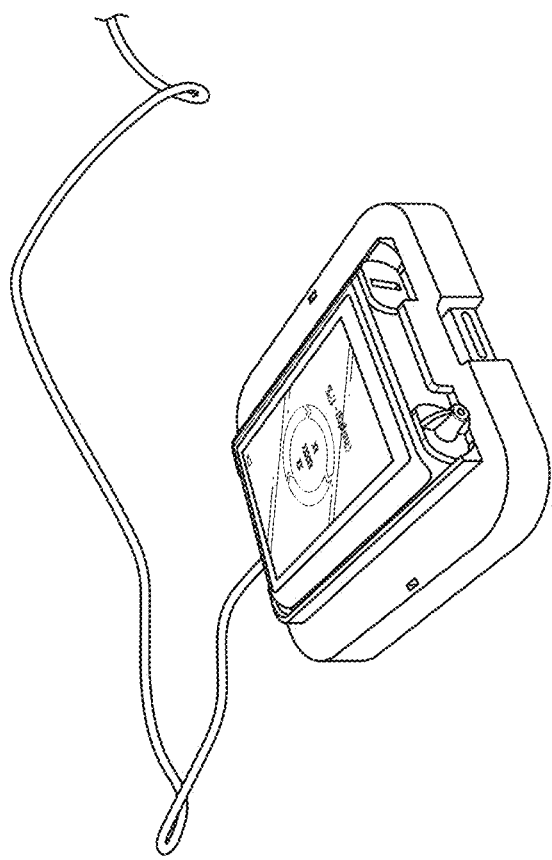

FIGS. 38 and 39 provide an example of a valve within the cartridge connector. In some embodiments, the valve is a flapper valve, in others it is not. In some embodiments, the valve is pre-loaded onto the valve seat of the body by the pre-load rib of the knob. In some embodiments, the valve is a constructed of a flexible material such as silicone. In some embodiments, the pre-load rib of the knob deforms the flat flapper valve disk as the disk is pressed against the valve seat of the body. In some embodiments, a seal is created between the valve and the valve seat.

In some embodiments, the flow path is as follows. In some embodiments, fluid flows up the needle (from the drug cartridge). In some embodiments, the fluid exits the needle below the valve filling the space. In some embodiments, when sufficient fluid pressure is generated by the plunger of the cartridge pushing out the fluid, then the perimeter of the valve cracks open to relieve the pressure. In some embodiments, the fluid gathers on the top side of the valve and flows through slots arranged around the pre-load rib. In some embodiments, the fluid then flows up the tube on its way to the patient. In some embodiments, the valve provides checked flow, where in the event that the fluid attempts to flow the other direction (i.e. from the tube back into the drug cartridge), the valve will remain closed stopping this flow.

In some embodiments, the valve is a ring valve. In some embodiments, the ring valve includes or consists of a silicone ring (labeled "tubing" in FIG. 40) that surrounds the knob side of the body. In some embodiments, the ring is pre-stretched around the body and covers a side hole that passes laterally out of the body. In some embodiments, when the pressure from the cartridge side exceeds the cracking pressure of the silicone ring, the ring separates from the body and allows fluid flow. Various views of ring valves are shown in FIGS. 40-43.

In some embodiments, the flow path through the ring valve is as follows. In some embodiments, fluid flows up the needle (from the drug cartridge). In some embodiments, the fluid abuts the ring valve. In some embodiments, when sufficient fluid pressure is generated by the plunger of the cartridge pushing out the fluid, then the perimeter of the ring valve cracks open to relieve the pressure. In some embodiments, the fluid then flows up the tube on its way to the patient. In some embodiments, the valve provides checked flow, where in the event that the fluid attempts to flow the other direction (i.e. from the tube back into the drug cartridge), the valve will remain closed stopping this flow.

In some embodiments, the plunger of the cartridge interacts with a drive nut of the pump (located in a pump chamber of a pump). As disclosed elsewhere herein, a cartridge connector attached to the cartridge may act to prevent inadvertent lift-off of the plunger from the drive nut. For example, in some embodiments, the check valve prevents the plunger from moving and distributing medicament in an uncontrolled and/or undesired way. For instance, medicament vials having plungers are typically designed to have little or no resistance and/or friction between the plunger and the wall of the reservoir. Thus, the plunger can move and distribute medicament with very little force applied to the plunger (e.g., even by moving the cartridge). In some embodiments, configurations described herein avoid issues with low friction plungers by using a check valve.

FIGS. 44-47 show views of another example of a cartridge connector including a check valve including standoff bumps and a fluid path flowing from the concave side of a check valve, around a proximal end of the check valve, and towards a convex side of the check valve. The check valve can be made of silicone or another material. In some embodiments, as shown, a modified sheath (e.g., cap feature) is provided over an entry port into the cartridge connector and under the knob. Fluid moves under the sheath via spaces made between the pictured standoff bumps (which are distributed around the sheath) the provide a path to the end of the cap feature. In some embodiments, fluid flows up the needle (from the drug cartridge). In some embodiments, the fluid abuts the sheath. In some embodiments, when sufficient fluid pressure is generated by the plunger of the cartridge pushing out the fluid, then the perimeter of the sheath opens to relieve the pressure. In some embodiments, the fluid then flows up the tube on its way to the patient. In some embodiments, the valve provides checked flow, where in the event that the fluid attempts to flow the other direction (i.e. from the tube back into the drug cartridge), the valve will remain closed stopping this flow.

Charger

In some embodiments, the pump contains an internal inductively chargeable battery. In some embodiments, the pump battery is not replaceable. In some embodiments, the pump is water resistant (up to 5 m, 10 m, 20 m, 50 m, or ranges including and/or spanning the aforementioned values) or water proof. In some embodiments, the pump is charged using an inductive charging pad/cradle and USB cable (as shown in FIGS. 48-51).

In some embodiments, to recharge your pump, one or more of the following steps can be performed: connect the wireless charging pad to the wall power outlet using the provided micro USB cable and plug, place the pump onto the supplied inductive charging pad, verify the touchscreen and the charging pad indicate that the pump is charging, and charge the pump with the supplied charging pad and cables.

In some embodiments, when placed on the charger, the touchscreen turns on and illuminates. In some embodiments, the touchscreen displays the state of charge and/or indicates that the pump is charging. In some embodiments, the light on the charging pad illuminates continuously while charging and blinks when it detects the presence of a pump but is not charging. In some embodiments, the pump indicates it is not charging and is not fully charged when the charging pad is blinking. In some embodiments, if the pump is not charging, the user can verify that the pump is properly aligned over the charging pad. In some embodiments, the typical time to fully charge a depleted battery is equal to or less than about 2 hours, 4 hours, or ranges including and/or spanning the aforementioned values.

In some embodiments, it may be beneficial to minimize the amount of time when the pump is without power. In some embodiments, when pump has no power, it will not be dosing insulin or providing the user with continuous glucose monitoring CGM values. In some embodiments, when the pump has run out of power, the Sleep/Wake button will not turn the screen on or off.

In some embodiments, for optimum battery life, it is recommended that you recharge the battery daily, regardless of what the battery level is reported as on the screen. In some embodiments, a fully charged battery can run several days for a typical user, but is dependent on amount of usage, especially of the backlight and volume of insulin delivered. In some embodiments, the user should monitor the battery charge level and alarms to determine what is a typical battery life for the user. In some embodiments, the user should recharge the pump according to typical usage.

In some embodiments, the system includes a wireless charging interface that conforms to a Qi standard. In some embodiments, the wireless charging include Rezence (from the AirFuel Alliance) and Open Dots (from the Open Dots Alliance).

Certain embodiments may comprise the following specifications:

| Specification Name | Specification |
| --- | --- |
| USB Wall Charger, P/N | Q3002-US, UL Listing E141650 |
| Input | 100 to 240 Volts AC 50/60 Hz, 0.8A Max |
| Output Voltage | 5 VDC/3.0 A, 9 VDC/2.0 A, 12 VDC/1.5 A |
| Output Connector | USB type A |
| Inductive Charging Pad w/USB Cable, P/N | TA511-S Choetech USB Cable USB A to USB Micro B, 1 Meter |
| Input Volt/Current | 5 Volts/2 A, 9 V/1.8 A |
| Output Power | 10W (Max) |
| Output Type | Qi Inductive Charger |
| Connector | USB Micro B |

Point of Care Cartridge Filling

In some embodiments (as in FIGS. 52-54), a cartridge may be filled at the point of care. An embodiment of such a point of care filling is shown in FIGS. 52-68, medicament is transferred from a vial 1400 containing the medicament (e.g., insulin) into the cartridge by way of a needle transfer hub 1401 and a pushrod 1402 that is connected to the elastomeric plunger 1403 residing in the cartridge 1404 by way of a breakable joint (not shown) or threads 1405 (shown in FIGS. 66 and 67) such that the pushrod 1402 can be disconnected and discarded (or reused) upon completion of the filling procedure.

Figures 52, 53, 54:
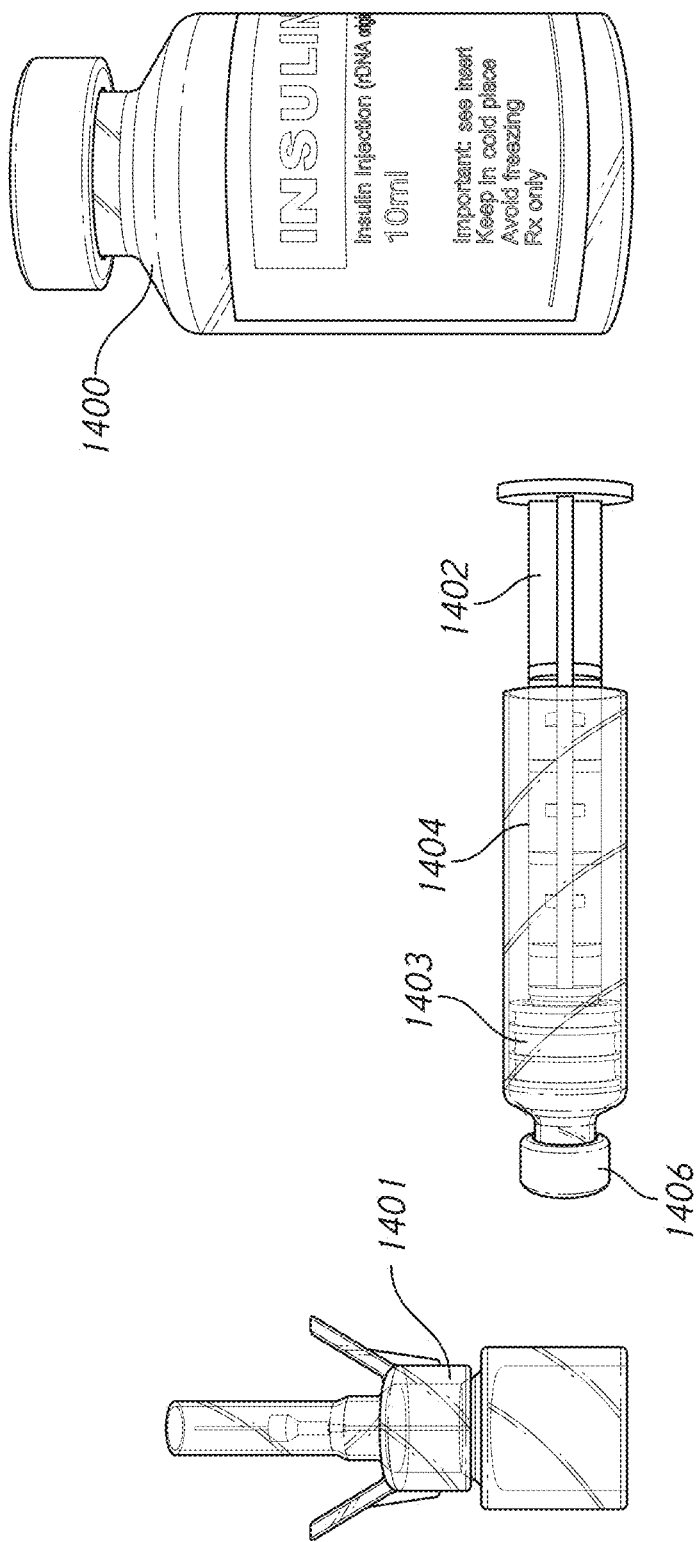
FIGS. 52-54 show embodiments of a vial, a transfer hub, and a cartridge.

Some embodiments, pertain to a method and components used to fill a vial at a point of care (e.g., by a doctor, nurse, or patient). In some embodiments, as shown in FIGS. 52-54, one or more of an empty medicament cartridge 1404 (or substantially empty from prior use), a medicament vial 1400, and a transfer hub are collected. In some embodiments, a pushrod 1402 is provided with the cartridge 1404 (when the cartridge is being filled a first time without prior use) and in other embodiments, the pushrod 1402 is engaged to the elastomeric plunger 1403 by a user before use. In some embodiments, the pushrod 1402 is engaged by threading it into a cavity of the plunger using threads on the pushrod.

Figure 57:
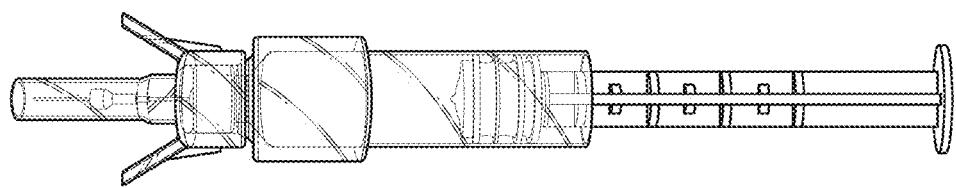
FIGS. 55-58 show embodiments of a transfer hub and a cartridge.
Figure 56:
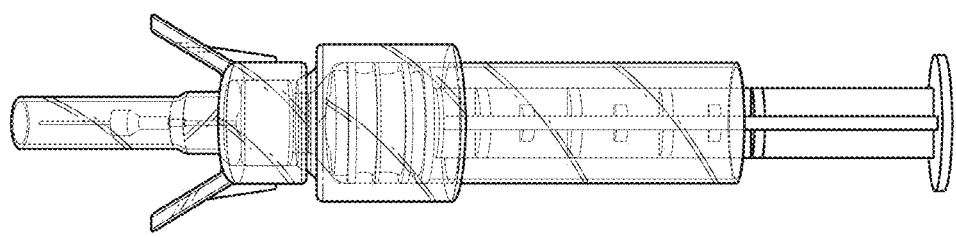
Figure 55:
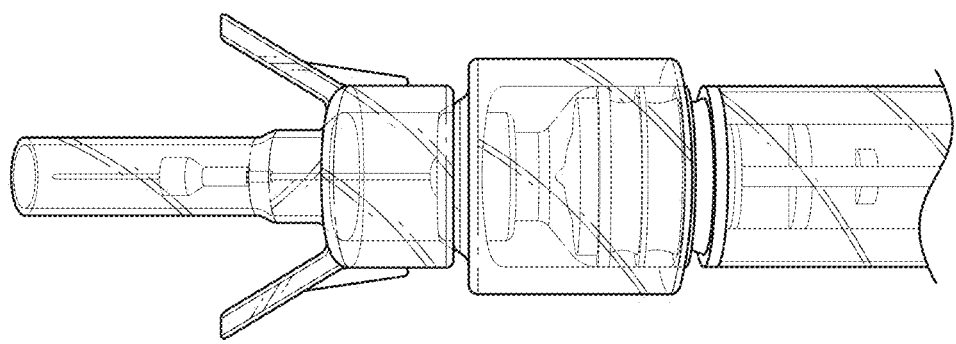
Figure 61:
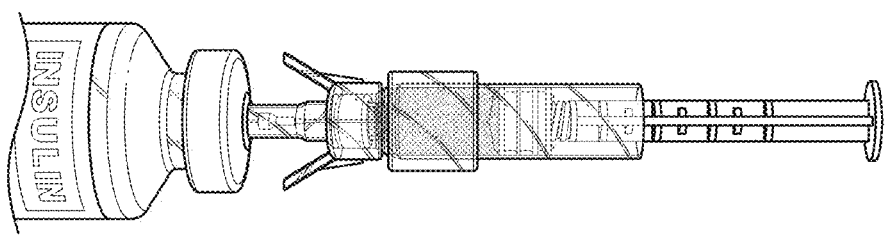
FIGS. 59-61 show embodiments of components for withdrawing medicament.
Figure 60:
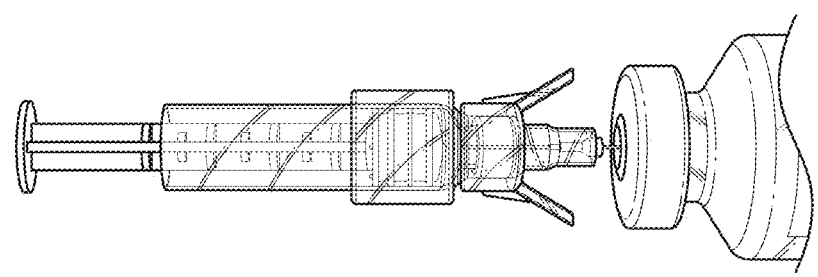
Figure 59:
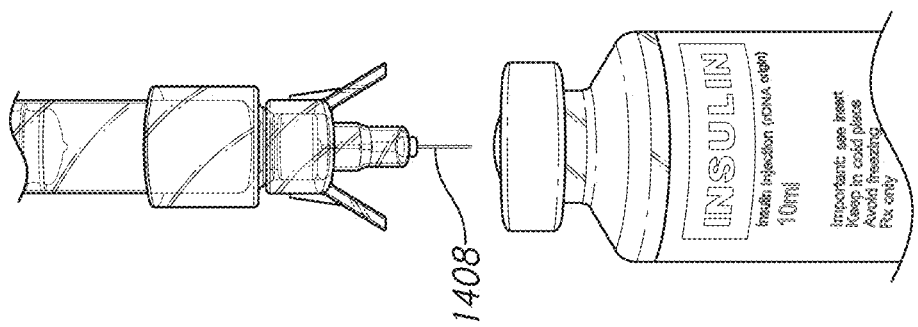
Figure 58:
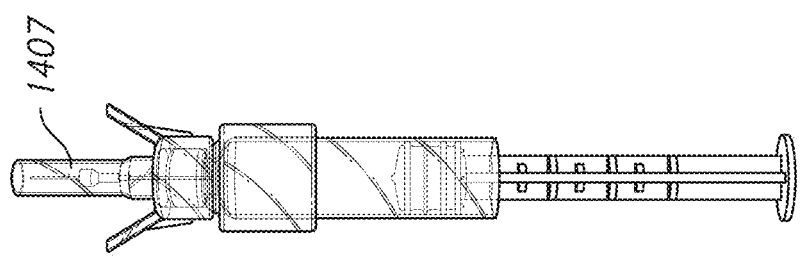
Figure 65:
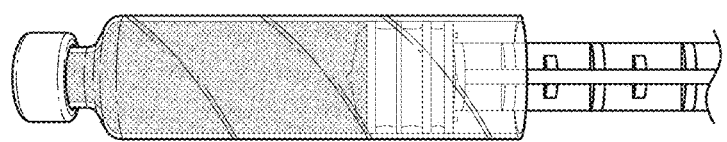
Figure 64:
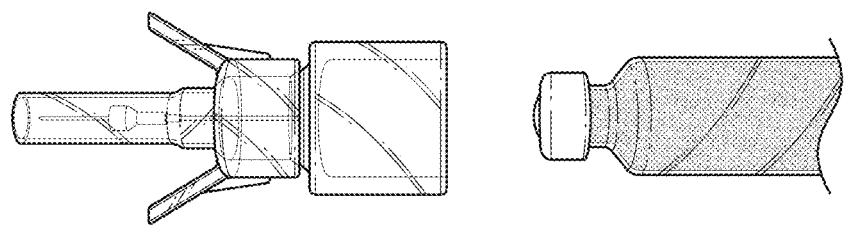
FIGS. 62-64 show embodiments of components for resheathing a needle.
Figure 63:
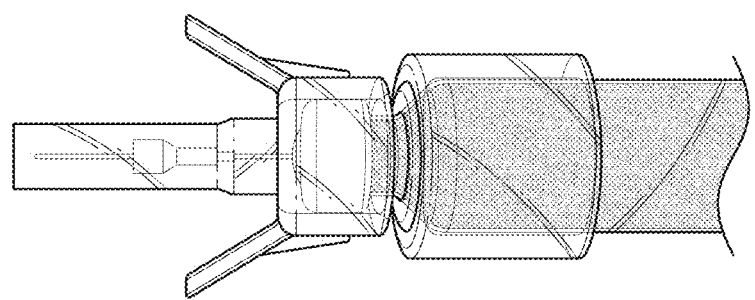
Figure 62:
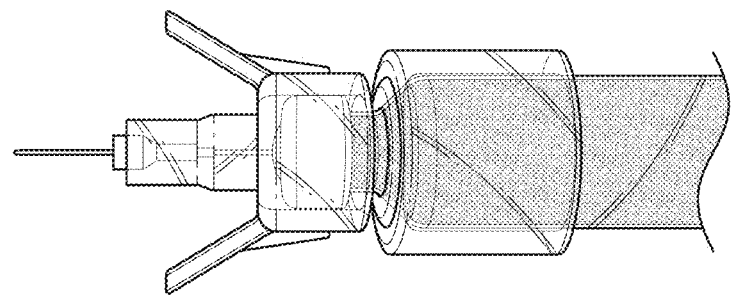

In some embodiments, as shown in FIGS. 55-58, the transfer hub 1401 is connected to a cap 1406 of the cartridge 1404. In some embodiments, once engaged to the plunger, the pushrod is withdrawn (as shown in FIGS. 56-58) to pull air into the cartridge 1404. In some embodiments, as shown in FIG. 59, the needle protector 1407 is removed from the needle 408, to expose the needle 1408. In some embodiments, the needle is used to then puncture a septum (or cap) of the vial 1400 and the air in the cartridge 1404 is pushed into the vial 400 to produce a positive pressure in the vial 1400. The medicament vial 1400 is then turned at an angle (e.g., upside down) to submerge the needle. The medicament is then withdrawn as shown in FIG. 61 into the cartridge 1404. The needle is then withdrawn and resheathed as shown in FIGS. 62-64. The pushrod is then removed as shown in FIGS. 65-67 to provide the filled medicament cartridge. The cartridge can be engaged to a cartridge connector and inserted into a pump.

In some embodiments, as disclosed herein, the pushrod can be connected directly to the plunger by means of a threads and, upon completion of the filling procedure, the pushrod can be disconnected and discarded (or reused), leaving the elastomeric plunger. In some embodiments, the threads could have a uni-directional burred surface (not shown) that would allow it to easily thread into the elastomeric plunger, but would resist being threaded out of the elastomeric plunger. In some embodiments, the pushrod has a thread-locking barb (not shown). In some embodiments, the pushrod and transfer hub are disposed of in a biohazard container as shown in FIG. 68.

O-Ring in Pump

As disclosed elsewhere herein, one general aspect includes an infusion pump (e.g., an infusion pump apparatus), the pump including a housing having an interior space. The infusion pump apparatus also includes a bore through said housing, said bore having a first end and a second end, and the bore configured to receive a medicament cartridge (e.g., a receptacle). In some embodiments, the infusion pump apparatus also includes where the first end defines an opening into said housing and the second end is located in the interior space of the housing. In some embodiments, the infusion pump apparatus also includes an elongate shaft disposed in the bore and configured to engage the medicament cartridge. In some embodiments, the infusion pump apparatus also includes an O-ring circumferentially disposed on the elongate shaft adjacent to the second end of the bore.

Implementations may include one or more of the following features. In some embodiments, the O-ring forms a barrier to water and debris from entering the interior space of the housing. In some embodiments, a position of the O-ring is configured to permit water or air movement around the medicament cartridge. In some embodiments, the O-ring is configured to permit pressure differential equalization between an infusion site and drug cartridge. In some embodiments, the O-ring exerts pressure on the elongated shaft when the O-ring is circumferentially disposed on the elongated shaft. In some embodiments, the O-ring further includes a lubricant to lubricate between the elongated shaft to reduce friction around between the O-ring and the elongated shaft.

In some embodiments, the O-ring is configured to maintain a pressure differential between ambient pressure and the interior space of the housing. In some embodiments, the O-ring is configured to maintain a pressure differential between the interior space of the housing and an interior of the bore. In some embodiments, the bore is configured to be exposed to an ambient pressure and equalize the ambient pressure. In some embodiments, the bore is configured to be exposed to an ambient pressure and equalize to the ambient pressure around the medicament cartridge. In some embodiments, the O-ring is compression fit over the on the elongate shaft is configured to create a barrier to water and air ingress into the interior space of the housing.

Infusion pumps may be adapted for implantation directly into the body of a patient. In some embodiments, the pump may be programmable to deliver a desired medicament from a cartridge directly to an infusion site based on various variables. Pressure differential, as well as permeation of air, water and debris particulates in the pump housing, may be advantageously managed by positioning an O-ring on the elongate shaft engaging the medicament cartridge. Accordingly, in an exemplary embodiment, an infusion pump apparatus comprises a housing and a bore through said housing. In some embodiments, the bore has a first end and a second end and is configured to receive a medicament cartridge. In some embodiments, the first end of the bore defines an opening into said housing. In some embodiments, the second end of the bore is located in the interior space of the housing. In some embodiments, an elongate shaft is disposed in the bore and configured to engage the medicament cartridge in the bore. In some embodiments, an O-ring is circumferentially disposed on the elongate shaft adjacent to the second end of the bore. In other embodiments, an elongate shaft disposed in the bore and configured to engage the medicament cartridge and an O-ring circumferentially disposed on the elongate shaft adjacent to the second end of the bore.

Figure 69:
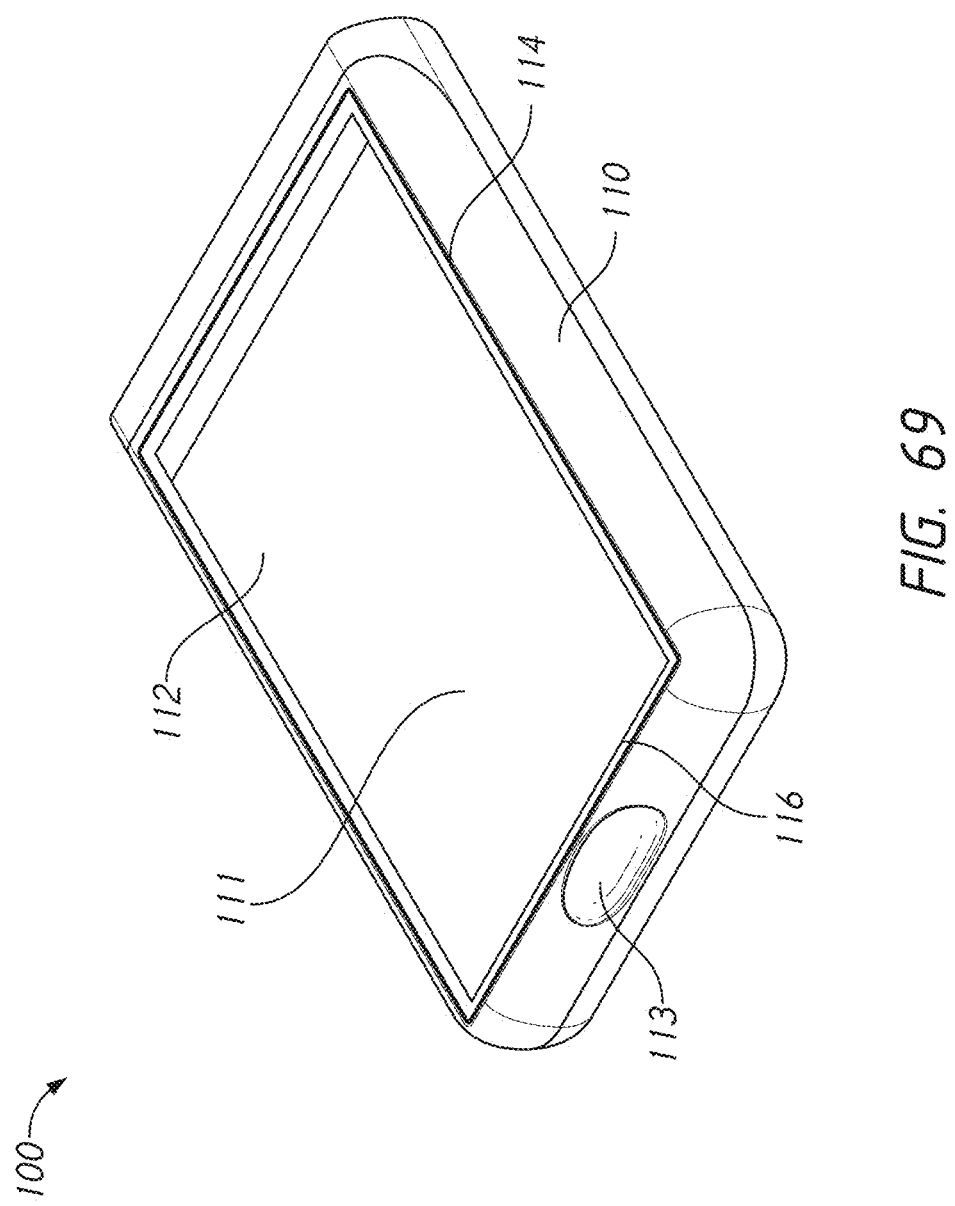
FIG. 69 shows a perspective view of an embodiment of an infusion pump housing.
Figure 70:
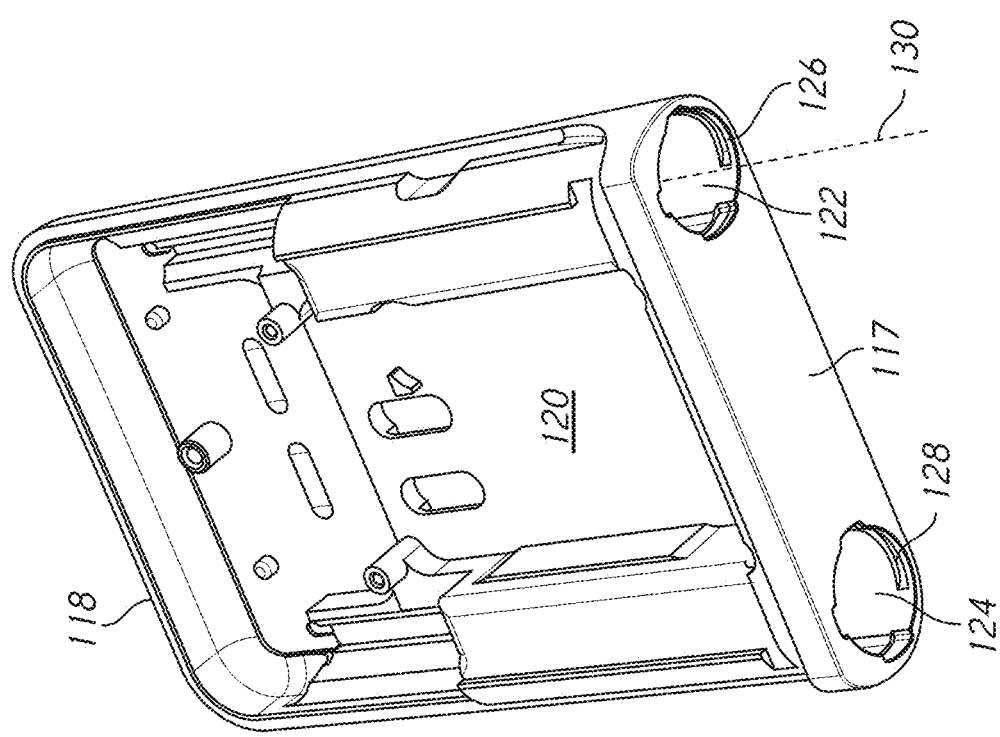
FIG. 70 shows a perspective view of an embodiment of an interior space of an infusion pump housing.
Figure 71:
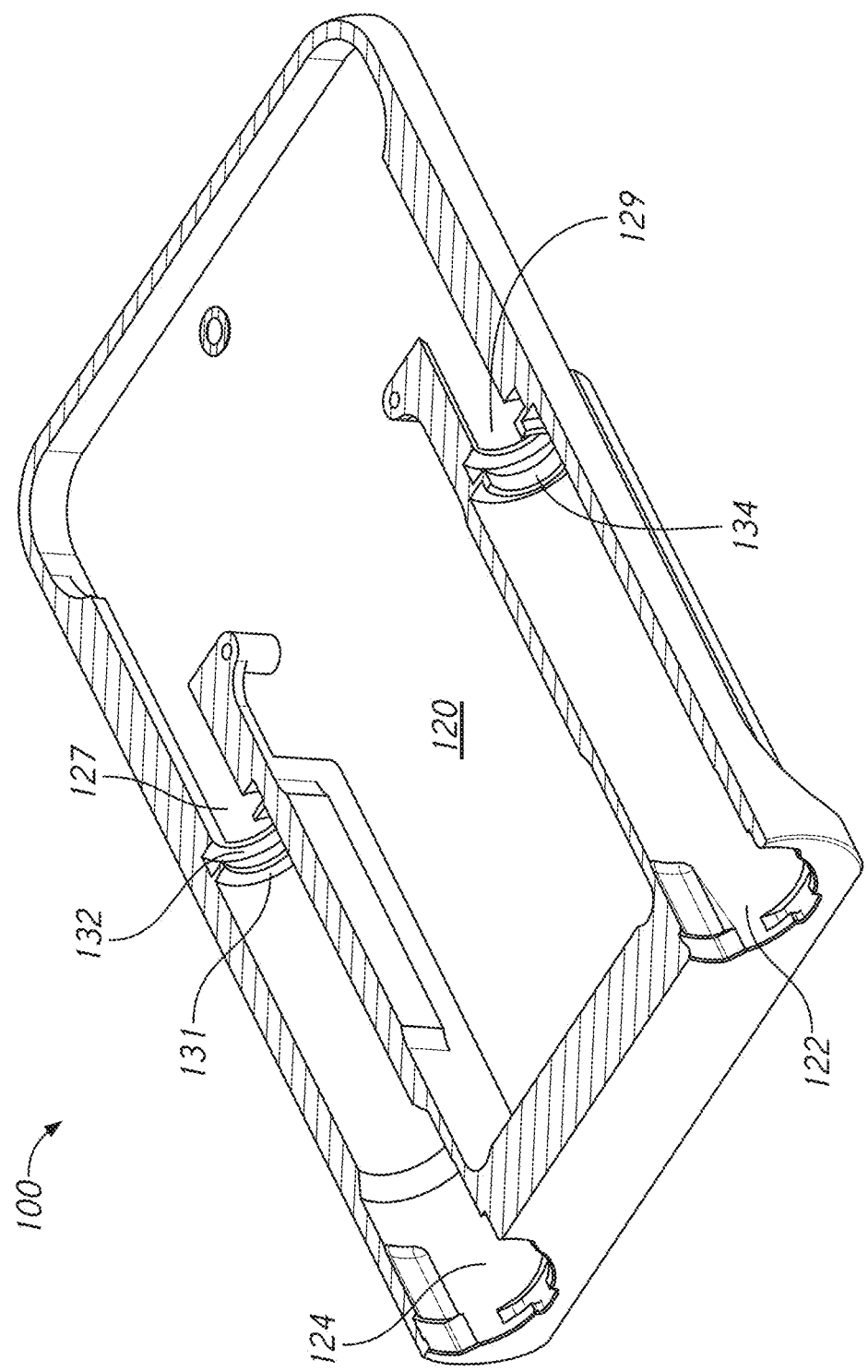
FIG. 71 shows a perspective view of an embodiment of an interior space of an infusion pump housing.
Figure 72:
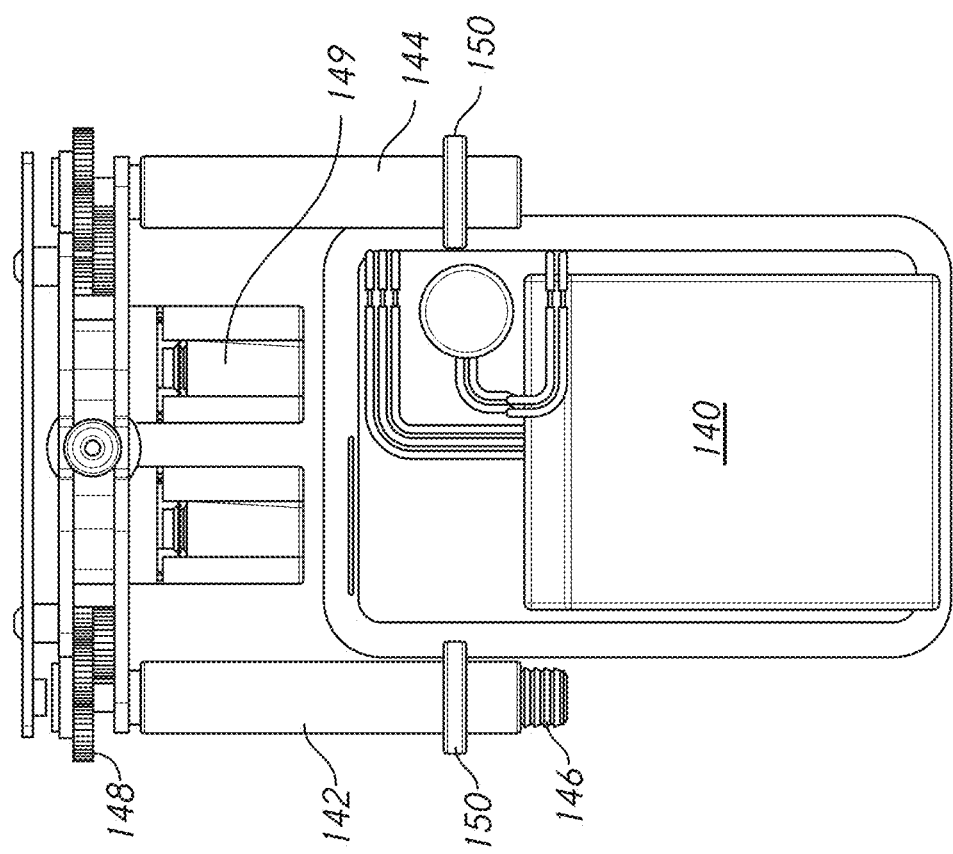
FIG. 72 shows a top view of embodiments of components in an infusion pump.
Figure 76:
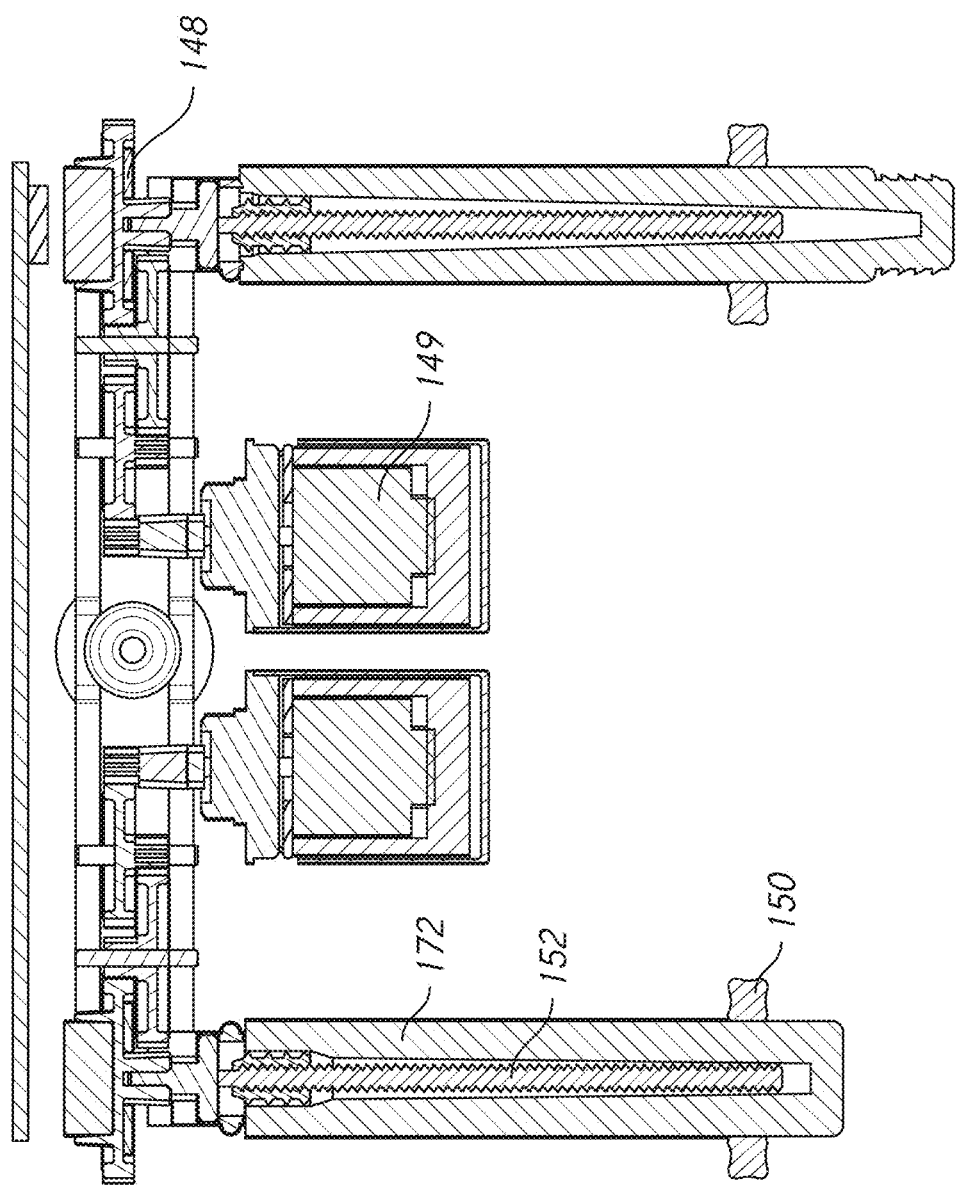
FIG. 76 shows a top cross-sectional view of embodiments of components of an infusion pump.
Figure 77:
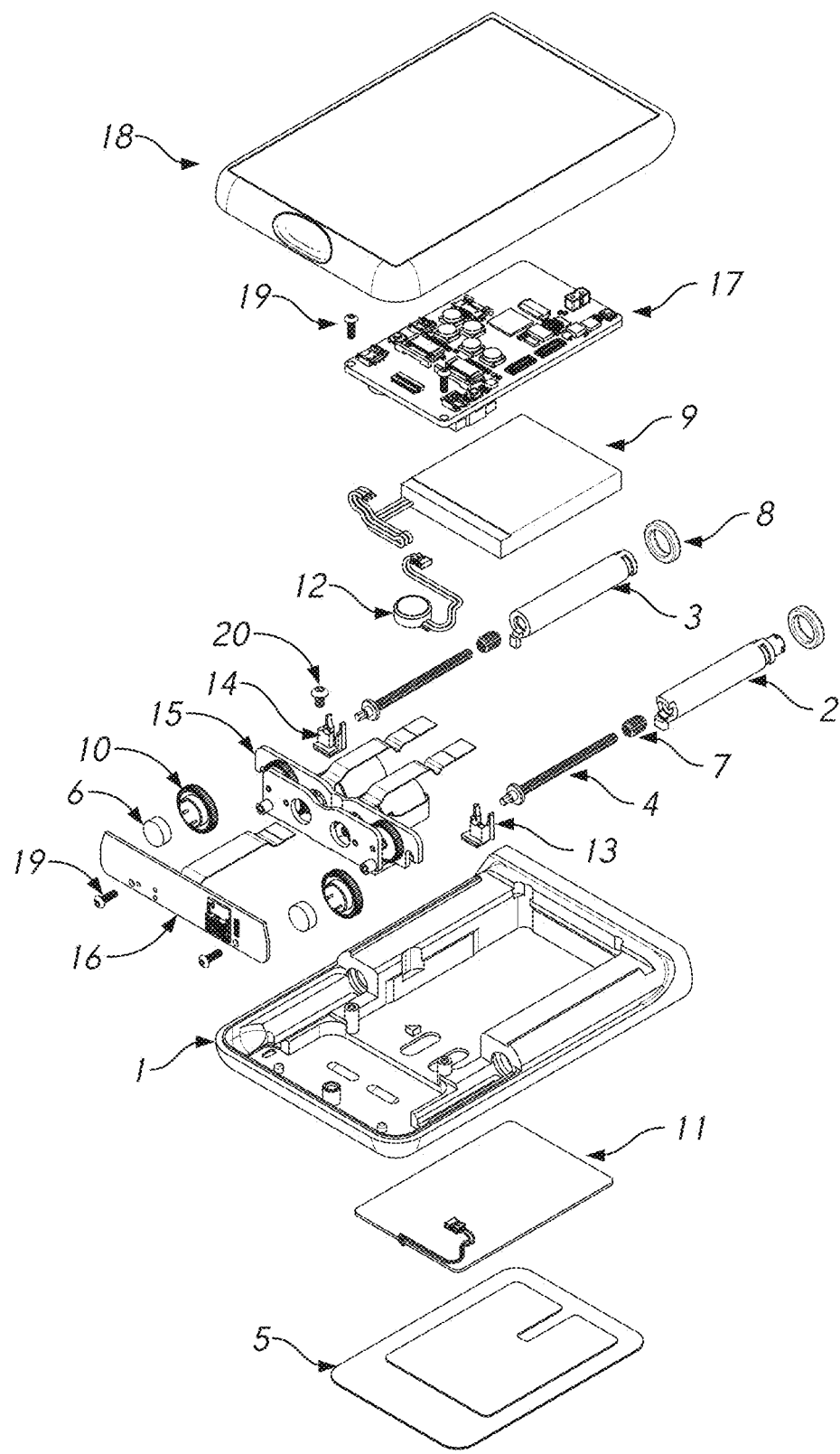
FIG. 77 shows an exploded view of embodiments of components of an infusion pump.

FIG. 69 is a perspective view of an infusion pump housing, according to an exemplary embodiment. FIG. 70 is a perspective view of the interior space of an infusion pump housing, according to an exemplary embodiment. FIG. 71 is a perspective view of the interior space of an infusion pump housing, according to an exemplary embodiment. FIG. 72 is a top view of components in an infusion pump, according to an exemplary embodiment. FIG. 73 is a perspective view of elongate shaft members of an infusion pump, according to an exemplary embodiment. FIG. 74 is a perspective view of two O-rings of an infusion pump, according to an exemplary embodiment. FIG. 75 is a cross-sectional view of elongate shaft members of an infusion pump, according to an exemplary embodiment. FIG. 76 is a top cross-sectional view of the components of an infusion pump, according to an exemplary embodiment. FIG. 77 is an exploded view of the components of an infusion pump, according to an exemplary embodiment.

Various embodiments include an IPX (water/dirt ingress) boundary sealing O-ring for an ambulatory medical device that has been designed in such a way to allow a drug cartridge to match the atmospheric pressure of the patient line and infusion site. In some embodiments, the IPX rating is greater than or equal to 1, 2, 3, 4, 5, 6, 7, 8, or ranges including and/or spanning the aforementioned values. In some embodiments, differences in atmospheric pressures between the infusion site and drug cartridge can lead to under/over delivery of a medicament. The drug cartridge chamber in the ambulatory medical device allows air and water to pass freely around the drug cartridges. This boundary choice requires the design drug cartridge chamber and drug cartridge to be impervious to the effects of the environment. The present disclosure uses some sort of sealing mechanism that prevents water from infiltrating the cartridge area, but still, allow air to move through the seal to equalize the pressure differential between the infusion site and drug cartridge. Typical designs that seal against the disposable device use O-rings to seal the pump surface to a flat surface on the disposable. One disadvantage of the previously mentioned design is that the sealing surface of the O-ring is exposed to the environment during set changes and can allow contamination to accumulate on the sealing surface of the O-ring causing the failure of the O-ring to provide adequate IPX sealing of the device. This can lead to seal failure and the ingress of water and fluids into the drug cartridge. The advantages of choosing the IPX seal boundary to not encompass allows the removal of the hydrophobic filter mechanism, as it is no longer needed. Water and air can freely move around the cartridge equalizing pressures. The O-ring seal thus provides the IPX seal to the device, preventing water and dirt from entering the electronic and motor/gear train enclosure. In some embodiments, the O-ring application around the lead screw nut provides a smooth continuous surface for sealing and prevents exposure of the sealing surface to environmental contaminants. In some embodiments, the wiping action of the O-ring against the lead screw nut prevents water and dust ingress into the enclosure and provides for a durable seal.

In the exemplary embodiments, the infusion pump apparatus comprises a housing for various components. The housing can essentially take any shape suitable for receiving a medicament cartridge and incorporating components for dispensing the medicament from the cartridge. An exemplary infusion pump is provided in FIG. 69. As shown, the infusion pump apparatus 100, comprises a housing 110 having a side portion 114, and the end portion 116 and top portion 112. The top portion 112 may be displayed. The housing exterior may further comprise input controls (not shown) for user input. The interior of the housing may be designed to retain or receive certain components. In the example shown in FIG. 70, the apparatus 100 has an interior space 120 as well as opposing top end 118 and an opposing bottom end 117.

In some embodiments, the infusion pump apparatuses of the exemplary embodiments may have one or more bores configured to receive a medicament cartridge. In general, the bores are cylindrical but may have any shape or modified features such as grooves or slots to receive features of a medicament cartridge as well as other components of the apparatus. FIG. 70 depicts an apparatus with two bores 122 and 124. Each bore has a first end (126, 128) and a second end (not shown), where the first end defines an opening into the said housing and the second end is located in the interior space of the housing. The first openings are located at the first ends 126 and 128 of each bore 122 and 124, respectively. Each bore has a longitudinal axis 130 along which other components translate (as further described below).

As shown in FIG. 71, the O-rings 150 are received by slots 132 and 134 that are located adjacent to the second ends 127 and 129 of the bores, respectively. Generally, the slots can take any shape that permits immobilizing the O-rings and forming a seal. For instance, the slots may be cylindrical and comprise a boundary which prevents the O-ring movement as the elongate shaft travels longitudinally in the bore. The slots 132 and 134 may have a raised surface 131 on both sides of the O-ring to immobilize the O-ring.

As shown in FIG. 72, the elongate shafts 142 and 144 which are disposed in the bores (not shown) may be driven by a motor 149 and gears 148 to translate longitudinally within the bore. The motors may be powered by a battery 140. In an exemplary embodiment, each elongate shaft comprises a lead screw and a lead screw nut (further described below) and engages a medicament cartridge (not shown). Moreover, as shown, one elongate shaft may further comprise a threaded portion 146 for identification. This feature advantageously allows a user to determine which bore holds a particular medicament cartridge when different cartridges (e.g., glucagon and insulin) are disposed in the device concurrently. Also, shown are O-rings 150 circumferentially disposed on each elongate shaft.

In some embodiments, the O-rings may be formed from any material suitable for achieving a seal and have different shape or thickness. In an exemplary embodiment, the O-ring for the elongate shaft comprises a polymeric material. Moreover, the O-rings can be of different sizes as exemplified in FIG. 74. Further, the O-ring can be compression fit over the elongate shaft to create a barrier to water and air ingress into the interior space of the housing.

As shown in FIG. 73, the O-rings 150 are placed adjacent to the first ends 157 and 159 of two elongate shafts 142 and 144, opposite the seconds ends 156 and 158, respectively. The elongate shafts 142 and 144 each comprise a lead screw 152, 154 threadedly engaged with the lead screw nut 172, 174 as shown in FIG. 75. Thus, as shown in FIG. 76, the motor 149 drives the gears 148 engaging the lead screw 152 gradually translates the lead screw nut 172 longitudinally towards the first end of the bore (not shown). Consequently, the O-ring, which is immobilized in the bore, remains in place yet still circumferentially disposed on the lead screw nut 172 portions of the elongate shaft during drug delivery.

In an exemplary embodiment, the O-ring seal exerts pressure on the elongated shaft when the O-ring is circumferentially disposed on the elongated shaft. A lubricant may be included to lubricate the elongated shaft to reduce the friction between the O-ring and the elongated shaft.

A non-limiting working example of an exemplary embodiment is provided in FIG. 77. As shown, the housing portion bottom portion 1 engages the housing top portion 18, which comprises a display. The back cover 5 is included to fully encase the housing. A battery 9 powers the PCBA main board and vibrator 12. O-rings 8 are placed on the lead screw nuts 2 and 3. The lead screw nut 2 is attached via a threaded insert 7 to the lead screw nut 3. The lead screw nut 2 engages a glucagon cartridge while lead screw nut 3 engages an insulin cartridge. The drive train assembly 15, and spur gear 10 act to mechanically actuate elongate shaft.

The features of the exemplary embodiments described in this disclosure provide various advantages. First, the O-ring seal around the elongate shaft forms a barrier to water and debris entering the interior space of the housing. This can prevent interference with the mechanical action of the pump and avoid potentially dispensing an incorrect amount of medicament.

Additionally, the position of the O-ring near the second end of the elongate shaft permits water or air movement around the cartridge whereby the pressure differential between the infusion site and the medicament cartridge is equalized.

Yet another advantage of the exemplary embodiments is that the infusion pump does not utilize an O-ring to seal the junction between the infusion set and the top of the medicament cartridge. In particular, the O-ring is not placed adjacent to the opening to the pump housing. This allows for a design which does not require a hydrophobic filter, as such filters become plugged, thereby affecting the pressure inside the pump housing. Moreover, a permanent installed hydrophobic filter would unlikely be able to last the full warranty period of the device, which forces the filter and complexity to be added to the disposable device which raises the costs and complexity on the disposable device.

The use of an O-ring as described can result in the pump apparatus being configured to maintain a pressure differential between the ambient pressure and the interior of the housing. Moreover, the pump apparatus can be configured to maintain a pressure differential between the interior of the housing and an interior of the bore.

Yet another advantage is that the Bore is configured to be exposed to the ambient pressure and equalize the ambient pressure around the medicament cartridge. Thus, a seal at the bore first opening is not required. Finally, the wiping action of the O-ring against the lead screw nut prevents water and dust ingress into the enclosure and provides a durable seal.

Example Methods and User Interfaces

An example pump can include a pump controller configured to implement one or more of the methods or user interfaces described herein. The pump can include a touchscreen that displays content and controls and accepts user input in the form of touches, taps, and/or other gestures. Certain example user interfaces that implement certain functions will be described herein; alternative user interfaces that accomplish the functions described herein and alternative or additional functions are possible. In some embodiments, a pump implements one, more than one, or all of the user interfaces, functionalities, and/or methods described herein.

A pump 100 can include a touchscreen 111 (see FIG. 69), a sleep/wake button 113 (see FIG. 69), an insulin cartridge port, and a glucagon cartridge port. The touchscreen can include a display layer capable of generating a capacitive touch sensitive layer capable of detecting a location of finger proximity or touch across a substantial portion of the display layer. A pump controller can generate commands for displaying content and/or controls on the touchscreen.

The sleep/wake button can be or include a capacitive touch interface that is positioned in a portion of the pump housing that is recessed from the area immediately surrounding the button. The button can have no external seams, thereby allowing the pump housing to have an uninterrupted surface in the vicinity of the button that is, for example, impervious to ingress of water into the housing. The button can be configured to sense a proximity or touch of a finger on or near a contact surface of the button (a "user touch"). In response sensing a user touch, a controller connected to the button 1006 can generate a command to cause the touchscreen to toggle on or off. In response to sensing a user touch that has a duration of at least 3 seconds (a "user touch and hold"), the controller can generate a command to turn on or toggle a backlight configured to illuminate the touchscreen.

The insulin cartridge port holds an insulin cartridge that can include an insulin cartridge connector for connecting the cartridge to an insulin tubing set leading to a dosing site. The glucagon cartridge port can include a chamber cover in the event that a glucagon cartridge is not installed. When the glucagon cartridge is installed, it can include a glucagon cartridge connector for connecting the cartridge to a glucagon tubing set leading to a dosing site that can be different from the insulin dosing site.

The pump can include a regulatory label and a device identifier.

Methods and user interfaces can be implemented by a pump controller connected to a touchscreen, including an example method for starting a pump, such as the pump. The starting method can be initiated, for example, when the user first charges the pump. In some embodiments, when a user places the pump on a charging pad for the first time, the touchscreen of the pump turns on, and a pump controller generates one or more displays that guide the user through the starting method.

The pump receives user input indicating that the starting method should be initiated. The pump receives a selection of a preferred language. The pump receives a device identifier selected by the user. The pump can receive confirmation or user selection of a current time. The pump can receive confirmation or user selection of a current date.

Methods and user interfaces can be implemented by a pump controller connected to a touchscreen, including: setting up a pump, such as the pump, to begin therapy of a subject; setting up a continuous glucose monitor (CGM); setting up or changing an insulin cartridge; setting up or changing an infusion site; and setting up a subject model including the weight of the subject and/or a parameter based on the weight of the subject.

Listing of user interfaces can be implemented by a pump controller connected to a touchscreen.

Methods and user interfaces can be implemented by a pump controller connected to a touchscreen, including: operation of a sleep/wake button, display of an unlock screen on a touchscreen, unlocking of a pump, display of a home screen on a touchscreen, and charging of a pump Methods and user interfaces can be implemented by a pump controller connected to a touchscreen, including: setting up a CGM; displaying information about a CGM session; setting CGM alerts; displaying CGM trends, values, and graphs; displaying CGM data and insulin delivery data; and displaying CGM communication status information.

Methods and user interfaces can be implemented by a pump controller connected to a touchscreen, including: changing an insulin cartridge, filling tubing, and changing an infusion site.

Methods and user interfaces can be implemented by a pump controller connected to a touchscreen, including: displaying a home screen; receiving blood glucose values measured by a blood glucose meter other than a CGM; pausing and resuming insulin delivery; receiving a selection of a volume level for alerts and other notifications; pairing a mobile electronic device to the pump; adjusting pump settings for therapy, time and date, device identifier, CGM alerts, and device power; adjusting clinical settings using a secret code; and displaying device history.

Methods and user interfaces can be implemented by a pump controller connected to a touchscreen, including receiving a meal announcement from a user.

At least some of the example methods and user interfaces can be implemented by a pump controller connected to memory that contains computer program instructions (grouped as modules or components in some embodiments) that a hardware processor can execute in order to implement one or more embodiments described herein. The memory can generally include RAM, ROM and/or other persistent, auxiliary or non-transitory computer-readable media. The memory can store an operating system that provides computer program instructions for use by the hardware processor in the general administration and operation of a pump, such as the pump described herein.

Terminology

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, user interfaces, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks, user interfaces, and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Language of example or capability used herein, such as, among others, "can," "could," "might," "may," "e.g.," "some," "certain," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Many variations may be made to the embodiments described herein. All variations are intended to be included within the scope of this disclosure. The description of the embodiments herein can be practiced in many ways. Any terminology used herein should not be construed as restricting the features or aspects of the disclosed subject matter. The scope should instead be construed in accordance with the appended claims.

What is claimed is:

1. A medicament infusion system for inductively charging a battery of an infusion pump configured to deliver medicaments to a patient, the medicament infusion system comprising:

an infusion pump assembly comprising:
  a pump housing;
  a first medicament chamber in the pump housing, the first medicament chamber comprising a first inlet port, the first medicament chamber configured to engage a first cartridge connector via the first inlet port of the first medicament chamber, the first medicament chamber being configured to engage the first cartridge connector to position a first medicament cartridge in the first medicament chamber, the first cartridge connector bonded to a first tube extending from the first cartridge connector, the first tube configured to channel a first medicament in the first medicament cartridge to the patient;
  a second medicament chamber in the pump housing, the second medicament chamber comprising a second inlet port, the second medicament chamber configured to engage a second cartridge connector via the second inlet port of the second medicament chamber, the second medicament chamber being configured to engage the second cartridge connector to position a second medicament cartridge in the second medicament chamber, the second cartridge connector bonded to a second tube extending from the second cartridge connector, the second tube configured to channel a second medicament in the second medicament cartridge to the patient; and
  an inductively chargeable battery assembly comprising a battery configured to power one or more motors for delivering the first and second medicaments to the patient from the first and second medicament cartridges via the first and second tubes, respectively; and an inductive charging pad comprising:
  an inductive charging circuit configured to transmit power to charge the battery of the infusion pump assembly;
  a pad housing comprising a docking area for the pump housing, the inductive charging circuit positioned in the pad housing, the pad housing comprising:
    a first flange extending from the pad housing perpendicular to a surface of the pad housing about the docking area, the first flange configured to engage a first side of the pump housing to position the pump housing relative to the docking area for the inductive charging circuit to transmit power to charge the battery of the infusion pump assembly;
    a second flange extending from the pad housing perpendicular to the surface of the pad housing about the docking area, the second flange configured to engage a second side of the pump housing to position the pump housing relative to the docking area for the inductive charging circuit to transmit power to charge the battery of the infusion pump assembly, the second side of the pump housing opposite the first side of the pump housing, the second flange extending along the surface of the pad housing about the docking area parallel to the first flange, wherein the first and second flanges are configured to engage the first and second sides of the pump housing to position the first and second sides of the pump housing against the first and second flanges, respectively; and
    a third flange extending from the pad housing perpendicular to the surface of the pad housing about the docking area, the third flange configured to engage a third side of the pump housing to position the pump housing relative to the docking area for the inductive charging circuit to transmit power to charge the battery of the infusion pump assembly, the third side of the pump housing extending between the first and second sides of the pump housing, the third flange extending along the surface of the pad housing about the docking area perpendicular to the first and second flanges, wherein the third flange is spaced from the first and second flanges to provide a first opening and a second opening, respectively, the first opening positioned between the first flange and the third flange to provide space for the first cartridge connector to extend through the first opening with the pump housing aligned relative to the docking area for the inductive charging circuit to transmit power to charge the battery of the infusion pump assembly, the second opening positioned between the second flange and the third flange to provide space for the second cartridge connector to extend through the second opening with the pump housing aligned relative to the docking area for the inductive charging circuit to transmit power to charge the battery of the infusion pump assembly, and wherein the first flange is spaced from the second flange to provide a third opening between the first and second flange to expose a fourth side of the pump housing, the fourth side opposite the third side of the pump housing.

2. The medicament infusion system of claim 1, wherein the first flange comprises a first extension from the first flange toward the second flange into the third opening about the docking area, and the second flange comprises a second extension from the second flange toward the first flange into the third opening about the docking area, wherein the first and second extensions are configured to engage the fourth side of the pump housing to position the third side of the pump housing against the third flange.

3. The medicament infusion system of claim 1, wherein each of the first, second, and third flanges have a vertical extent from the surface of the pad housing less than a corresponding vertical extent of each of the first, second, and third sides of the pump housing, respectively, with the pump housing aligned relative to the docking area for the inductive charging circuit to transmit power to charge the battery of the infusion pump assembly.

4. The medicament infusion system of claim 1, wherein the pad housing comprises an indentation in the surface of the pad housing, the indentation positioned between the first, second, and third flanges corresponding to the docking area to facilitate alignment of the pump housing relative to the docking area for the inductive charging circuit to transmit power to charge the battery of the infusion pump assembly.

5. The medicament infusion system of claim 1, wherein the infusion pump assembly comprises a sleep/wake button on the fourth side of the pump housing, wherein the sleep/wake button is between the first and second flanges in the third opening with the pump housing aligned relative to the docking area for the inductive charging circuit to transmit power to charge the battery of the infusion pump assembly.

6. The medicament infusion system of claim 1, wherein the infusion pump assembly comprises a screen positioned between the first, second, third, and fourth sides of the pump housing, the pad housing configured to position the pump housing for the screen to face away from the docking area, the infusion pump assembly configured to indicate on the screen a charging state of the battery with the pump housing aligned relative to the docking area for the inductive charging circuit to transmit power to charge the battery of the infusion pump assembly.

7. A medicament infusion inductive charging pad for inductively charging a battery of an infusion pump configured to deliver a medicament to a patient, the medicament infusion inductive charging pad comprising:

an inductive charging circuit configured to transmit power to charge a battery of an inductively chargeable battery assembly of an infusion pump configured to deliver a medicament to a patient; and a pad housing, the inductive charging circuit positioned in the pad housing, the pad housing comprising:

a first flange extending from the pad housing perpendicular to a surface of the pad housing, the first flange configured to engage a first side of a pump housing of the infusion pump having the battery to position the pump housing relative to the pad housing for the inductive charging circuit to transmit power to charge the battery of the infusion pump; and a second flange extending from the pad housing perpendicular to the surface of the pad housing, the second flange configured to engage a second side of the pump housing to position the pump housing relative to the pad housing for the inductive charging circuit to transmit power to charge the battery of the infusion pump, the second side of the pump housing extending perpendicular to the first side of the pump housing, the second flange extending along the surface of the pad housing perpendicular to the first flange, wherein the second flange is spaced from the first flange to provide a first opening, the first opening positioned between the first flange and the second flange to provide space for a first cartridge connector of the infusion pump to be positioned in the first opening with the pump housing aligned relative to the pad housing for the inductive charging circuit to transmit power to charge the battery of the infusion pump.

8. The medicament infusion inductive charging pad of claim 7, wherein the pad housing comprises a third flange extending from the pad housing perpendicular to the surface of the pad housing, the third flange configured to engage a third side of the pump housing to position the pump housing relative to the pad housing for the inductive charging circuit to transmit power to charge the battery of the infusion pump, the third side of the pump housing opposite the first side of the pump housing, the third flange extending along the surface of the pad housing parallel to the first flange, wherein the first and third flanges are configured to engage the first and third sides of the pump housing to position the first and third sides of the pump housing against the first and third flanges, respectively, wherein the first flange is spaced from the third flange to provide a second opening between the first and third flanges to expose a fourth side of the pump housing, the fourth side opposite the second side of the pump housing.

9. The medicament infusion inductive charging pad of claim 8, wherein the second flange is spaced from the third flange to provide a third opening, the third opening positioned between the second flange and the third flange to provide space for a second cartridge connector of the infusion pump to be positioned in the third opening with the pump housing aligned relative to the pad housing for the inductive charging circuit to transmit power to charge the battery of the infusion pump.

10. The medicament infusion inductive charging pad of claim 8, wherein the first flange comprises a first extension from the first flange toward the third flange into the second opening, and the third flange comprises a second extension from the third flange toward the first flange into the second opening, wherein the first and second extensions are configured to engage the fourth side of the pump housing to position the second side of the pump housing against the second flange.

11. The medicament infusion inductive charging pad of claim 7, wherein the first flange comprises an extension from the first flange extending parallel to the second flange, wherein the extension is configured to engage a fourth side of the pump housing to position the second side of the pump housing against the second flange, the fourth side opposite the second side of the pump housing.

12. The medicament infusion system of claim 7, wherein the first flange has a vertical extent from the surface of the pad housing less than a vertical extent of the first side of the pump housing with the pump housing aligned relative to the pad housing for the inductive charging circuit to transmit power to charge the battery of the infusion pump.

13. The medicament infusion system of claim 7, wherein the first cartridge connector of the infusion pump is connected to a tube extending from the pump housing configured to attach to the patient and to channel the medicament to the patient, wherein the tube extends through the first opening with the pump housing aligned relative to the pad housing for the inductive charging circuit to transmit power to charge the battery of the infusion pump.

14. A medicament infusion inductive charging pad for inductively charging a battery of an infusion pump configured to deliver medicaments to a patient, the medicament infusion inductive charging pad comprising:
an inductive charging circuit configured to transmit power to charge a battery of an inductively chargeable battery assembly of an infusion pump configured to deliver medicaments to a patient; and
a pad housing, the inductive charging circuit positioned in the pad housing, the pad housing comprising:
a first flange extending from the pad housing perpendicular to a surface of the pad housing, the first flange configured to engage a first side of a pump housing of the infusion pump having the battery to position the pump housing relative to the pad housing for the inductive charging circuit to transmit power to charge the battery of the infusion pump; and
a second flange extending from the pad housing perpendicular to the surface of the pad housing, the second flange configured to engage a second side of the pump housing to position the pump housing relative to the pad housing for the inductive charging circuit to transmit power to charge the battery of the infusion pump, the second side of the pump housing opposite the first side of the pump housing, the second flange extending along the surface of the pad housing parallel to the first flange, wherein the first and second flanges are configured to engage the first and second sides of the pump housing to position the first and second sides of the pump housing against the first and second flanges, respectively,
wherein the first flange is spaced from the second flange to provide a first opening between the first and second flange to expose a third side of the pump housing, the third side perpendicular to the first and second sides of the pump housing.

15. The medicament infusion inductive charging pad of claim 14, wherein the pad housing comprises a third flange extending from the pad housing perpendicular to the surface of the pad housing, the third flange configured to engage a fourth side of the pump housing to position the pump housing relative to the pad housing for the inductive charging circuit to transmit power to charge the battery of the infusion pump, the fourth side opposite the third side of the pump housing, the third flange extending along the surface of the pad housing perpendicular to the first and second flanges.

16. The medicament infusion inductive charging pad of claim 15, wherein the third flange is spaced from the first and second flanges to provide a second opening and a third opening, respectively, the second opening positioned between the first flange and the third flange to provide space for a first cartridge connector of the infusion pump to be positioned in the second opening with the pump housing aligned relative to the pad housing for the inductive charging circuit to transmit power to charge the battery of the infusion pump, the third opening positioned between the second flange and the third flange to provide space for a second cartridge connector of the infusion pump to be positioned in the third opening with the pump housing aligned relative to the pad housing for the inductive charging circuit to transmit power to charge the battery of the infusion pump.

17. The medicament infusion inductive charging pad of claim 16, wherein the first cartridge connector of the infusion pump is connected to a first tube extending from the pump housing and configured to attach to the patient and to channel a first medicament to the patient, wherein the second cartridge connector of the infusion pump is connected to a second tube extending from the pump housing configured to attach to the patient and to channel a second medicament to the patient, wherein the first and second tubes extend through the second and third openings, respectively, with the pump housing aligned relative to the pad housing for the inductive charging circuit to transmit power to charge the battery of the infusion pump.

18. The medicament infusion inductive charging pad of claim 14, wherein the first flange comprises a first extension from the first flange toward the second flange into the first opening between the first and second flanges, and the second flange comprises a second extension from the second flange toward the first flange into the first opening, wherein the first and second extensions are configured to engage the third side of the pump housing to position the pump housing relative to the pad housing for the inductive charging circuit to transmit power to charge the battery of the infusion pump.

19. The medicament infusion inductive charging pad of claim 14, wherein the first and second flanges each have a vertical extent from the surface of the pad housing less than a corresponding vertical extent of the first and second sides of the pump housing, respectively, with the pump housing aligned relative to the pad housing for the inductive charging circuit to transmit power to charge the battery of the infusion pump.

20. The medicament infusion inductive charging pad of claim 14, wherein the pad housing comprises an indentation in the surface of the pad housing, the indentation positioned between the first and second flanges to facilitate aligning the pump housing relative to the pad housing for the inductive charging circuit to transmit power to charge the battery of the infusion pump.

* * * * *

UNITED STATES PATENT AND TRADEMARK OFFICE
CERTIFICATE OF CORRECTION

PATENT NO. : 11,278,661 B2
APPLICATION NO. : 16/814925
DATED : March 22, 2022
INVENTOR(S) : David Matthew Henderson et al.

It is certified that error appears in the above-identified patent and that said Letters Patent is hereby corrected as shown below:

On the Title Page

On Page 5, Column 2, Line 10, under Other Publications, delete "marekt," and insert --market,--.

In the Specification

In Column 6, Line 50, delete "o-ring" and insert --O-ring--.

In Column 8, Line 2, delete "knob" and insert --knob.--.

In Column 11, Line 40, delete "TA511-S" and insert --TS511-S--.

In Column 17, Line 24, delete "pump" and insert --pump.--.

In the Claims

In Column 23, Claim 12, Line 8, delete "system" and insert --inductive charging pad--.

In Column 23, Claim 13, Line 14, delete "system" and insert --inductive charging pad--.

Signed and Sealed this
Twelfth Day of July, 2022

Katherine Kelly Vidal
*Director of the United States Patent and Trademark Office*